(12) United States Patent
Zillmann et al.

(10) Patent No.: US 11,326,154 B2
(45) Date of Patent: May 10, 2022

(54) SOLUBLE INTEIN FUSION PROTEINS AND METHODS FOR PURIFYING BIOMOLECULES

(71) Applicant: Merck Patent GmbH, Darmstadt (DE)

(72) Inventors: Martin Zillmann, Burlington, MA (US); Joe Orlando, Burlington, MA (US)

(73) Assignee: Merck Patent GmbH, Darmstadt (DE)

( * ) Notice: Subject to any disclaimer, the term of this patent is extended or adjusted under 35 U.S.C. 154(b) by 164 days.

(21) Appl. No.: 16/388,193

(22) Filed: Apr. 18, 2019

(65) Prior Publication Data

US 2019/0241609 A1 Aug. 8, 2019

Related U.S. Application Data

(63) Continuation of application No. 15/511,908, filed as application No. PCT/US2015/057125 on Oct. 23, 2015, now Pat. No. 10,308,679.

(Continued)

(51) Int. Cl.
| | |
|---|---|
| *C07K 1/22* | (2006.01) |
| *C12P 21/00* | (2006.01) |
| *C12N 11/08* | (2020.01) |
| *C12N 11/14* | (2006.01) |
| *C12N 9/50* | (2006.01) |
| *C07K 16/00* | (2006.01) |
| *C07K 14/00* | (2006.01) |
| *C12N 9/52* | (2006.01) |

(Continued)

(52) U.S. Cl.
CPC ............... *C12N 9/52* (2013.01); *C07K 1/22* (2013.01); *C07K 14/00* (2013.01); *C07K 16/00* (2013.01); *C12N 9/93* (2013.01); *C12N 11/082* (2020.01); *C12N 11/14* (2013.01); *C12P 21/00* (2013.01); *C07K 2319/92* (2013.01)

(58) Field of Classification Search
None
See application file for complete search history.

(56) References Cited

U.S. PATENT DOCUMENTS

| | | | |
|---|---|---|---|
| 2002/0106693 A1* | 8/2002 | Manfredi | C12N 15/1055 435/7.1 |
| 2002/0106699 A1 | 8/2002 | Manfredi et al. | |

(Continued)

FOREIGN PATENT DOCUMENTS

| | | |
|---|---|---|
| CN | 101884910 | 11/2010 |
| CN | 104053779 A | 9/2014 |

(Continued)

OTHER PUBLICATIONS

Ericsson, J; etal; "Synthesis of hydrophilic poly(vinyl ether)s and their application for separation media design" Reactive & Functional Polymers, 30, 327-340, 1996 (Year: 1996).*

(Continued)

*Primary Examiner* — David W Berke-Schlessel
(74) *Attorney, Agent, or Firm* — EMD Millipore Corporation

(57) ABSTRACT

The present invention relates to fusion proteins comprising an N-intein polypeptide and an N-intein solubilization partner, and affinity chromatography matrices comprising such fusion proteins, as well as methods of using same.

9 Claims, 7 Drawing Sheets
(1 of 7 Drawing Sheet(s) Filed in Color)
Specification includes a Sequence Listing.

Related U.S. Application Data

(60) Provisional application No. 62/209,010, filed on Aug. 24, 2015, provisional application No. 62/074,494, filed on Nov. 3, 2014.

(51) Int. Cl.
*C12N 9/00* (2006.01)
*C12N 11/082* (2020.01)

(56) References Cited

U.S. PATENT DOCUMENTS

| | | |
|---|---|---|
| 2008/0255027 A1 | 10/2008 | Moya et al. |
| 2017/0291919 A1 | 10/2017 | Zillmann et al. |

FOREIGN PATENT DOCUMENTS

| | | |
|---|---|---|
| JP | 2002-541066 A | 12/2002 |
| JP | 2003-523503 A | 8/2003 |
| JP | 2012-520064 A | 9/2012 |
| JP | 2013-235011 A | 11/2013 |
| JP | 2014-528720 A | 10/2014 |
| WO | 01/51927 A1 | 7/2001 |
| WO | WO 2008/091740 | 7/2008 |
| WO | WO 2013/045632 | 4/2013 |
| WO | 2014/004336 A2 | 1/2014 |
| WO | WO 2014/191455 | 12/2014 |
| WO | 2016069774 A1 | 5/2016 |
| WO | WO 2014/110393 | 7/2017 |

OTHER PUBLICATIONS

He, Jincan; et al.; "Magnetic separation techniques in sample preparation for biologicalanalysis: A review" Journal of Pharmaceutical and Biomedical Analysis, 101, 84-101, 2014 (Year: 2014).*
Liu, Xiang-Qin; "Protein Splicing Intein: Genetic Mobility, Origin, and Evolution" Annual Review of Genetics, 34, 61-76, 2000 (Year: 2000).*
Wagner, Ingrid; Musso, Hans; "New Naturally Occurring Amino Acids" Angewandte Chemie International Edition in English, 22, 816-828, 1983 (Year: 1983).*
Gp41.1 N-terminal intein having fusion protein (G1 N), SEQ ID 2, retrieved from EBI accession No. GSP: BAM89804, May 23, 2013. Solubility optimized iProtease related gp41-1 N-intein, SEQ 14, (Jun. 30, 2016).
Wei, L., et al. "Split intein facilitated tag affinity purification for recombinant proteins with controllable tag removal by inducible auto-cleavage", Journal of Chromatography A, 1218 (2011) 2553-2560.
Partial European Search Report for Application No. 19169588.1, "Soluble Intein Fusion Proteins and Methods for Purifying Biomolecules", dated Jul. 15, 2019.
Altschul et al., "Basic local alignment search tool", *J. Mol. Biol.*, 215(3): 403-410 (1990).
Aranko, A.S., et al., et al., "In Vivo and In Vitro Protein Ligation by Naturally Occurring and Engineered Split DnaE Inteins", *PLoS ONE*, 4(4): e5185 (2009).
Arshady, R., "Styrene Based Polymer Supports Developed by Suspension Polymerization", *Chimica e L'Industria*, 70(9): 70-75 (1988).
Carvajal-Vallejos P., et al., , "Unprecedented Rates and Efficiencies Revealed for New Natural Split Inteins from Metagenomic Sources", *J. Biol. Chem.* 287 (34): 28686-28696 (2012).
Caspi, et al., "Distribution of split DnaE inteins in Cyanobacteria", *Mol. Microbiol.*, 50(5): 1569-1577 (2003).
Choi, J., et al., "Protein Trans-splicing and Characterization of a Aplit Family B-type DNA Polymerase from the Hyperthermophilic Archaeael Parasite *Nanoarchaeum equitans*" *J. Mol. Biol.*, 556: 1093-1106(2006).
Costa, S., et al., "Fusion tags for protein solubility, purification, and immunogenicity in *Escherichia coli*: the novel Fh8 system", *Frontiers in Microbiology*, 5(63): 1-20 (Feb. 2014).

Dassa, B., et al., "Fractured genes: a novel genomic arrangement involving new split inteins and a new homing endonuclease family", *Nucl. Acids Res.*, 37(8): 2560-2573 (2009).
Dassa, B., et al., "Trans Protein Splicing of Cyanobacterial Split Inteins in Endogenous and Exogenous Combinations", *Biochemistry*, 46: 322-330 (2007).
Garbe, D., et al., "Protein trans-splicing on an M13 bacteriophage: towards directed evolution of a semisynthetic split intcin by phage display", *Journal of Peptide Science*, 2010, 16: 575-581.
Guan, D., et al., "Split Intein Mediated Ultra-Rapid Purification of Tagless Protein (SIRP)", *Biotech. Bioeng.*, 110(9): 2471-2481 (2013).
Hall, TA., "BioEdit: a user-friengly biological sequence alignment editor and analysis program for Windows 95/98/NT", *Nucl. Acids. Symp. Ser.*, 41: 95-98 (1999).
Henikoff & Henikoff, "Amino acid substitution matrices from protein blocks". *Proc. Natl. Acad. Sci. USA*, 89: 10915-10919 (1989).
Hjerten, S., "The Preparation of Agarose Spheres for Chromatography of Molecules and Particles", *Biochim Biophys Acta*, 79(2): 393-398 (1964).
Ikai, AJ., J. "Thernostability and Aliphatic Index of Globular Proteins", *Biochem.* 88: 1895 (1980).
Iwai, I., et al. "Highly efficient protein trans-splicing by a naturally split DnaE intein from *Nostoc punctiforme*" FEBS Letters 550: 1853-1858 (2006).
Kuznetsov, P.V., "Epoxy-Activated Adsorbents n Liquid Chromatography of Physiologically Active Substances", *Pharmaceutical Chemistry Journal*, 27: 439-52 (1993).
Kyte, J., et al., , "A Simple Method for Displaying the Hydropathic Character of a Protein", *J. Mol. Biol.*, 157: 105-132 (1982).
Liu, X. and Yang, J., "Split dnaE Genes Encoding Multiple Novel Inteins in *Trichodesmium erythraeum*", *J. Biol. Chem.*, 275: 26315-26318 (2003).
Ljungquist et al., "Thiol-directed immobilization of recombinant IgG-binding receptors", *Eur. J. Biochem*, 186: 558-561 (1989).
Lu, W., et al., "Split intein facilitated tag affinitv purification for recombinant proteins with controllable tag removal by inducible auto-cleavage", *J. Chrom. A*, 1218: 2553-2560 (2011).
Needleman & Wunsch, "*A General Method Applicable to the Search for Similarities in the Amino Acid Sequence of Two Proteins*", *J. Mol. Biol.*, 48: 443-453 (1970).
Notification Concerning Transmittal of International Preliminary Report on Patentability for International Application No. PCT/US2015/057125, "Soluble Intein Fusion Proteins and Methods for Purifying Biomolecules", dated Mar. 31, 2016, 10 pgs.
Notification of Transmittal of The International Search Report and The Written Opinion of the International Searching Authority for International Application No. PCT/US2015/057125, "Soluble Intein Fusion Proteins and Methods for Purifying Biomolecules", dated Mar. 31, 2016, 16 pgs.
Pearson & Lipman, "Improved tools for biological sequence comparison", *Proc. Nat'l. Acad. Sci. USA*, 85: 2444-2448 (1988).
Shah, N.H., et al., "Naturally Split Inteins Assemble through a "Capture and Collapse" Mechanism", *J. Amer. Chem. Soc.*, 2013, 135: 18673-18681.
Smith & Waterman, "Comparison of Biosequences", *Adv. Appl. Math.*, 2: 482-489 (1981).
Wang, Z., et al., "Ubiquitin-intein and SUM02-intein fusion systems for enhanced protein production and purification", *Protein Expression and Purification*, 82 (2012) 174-178.
Wilkinson, DL, et al. "Predicting the Solubility of Recombinant Proteins in *Escherichia coli*" *Bio/Technology*, 9: 443 (1991).
Wood, D., et al., "Intein Applications: From Protein Purification and Labeling to Metabolic Control Methods", *Journal of Biological Chemistry*, 289(21): 14512-14519 (May 23, 2014).
Wu, H., et al., "Protein trans-splicing by a split intein encoded in a split DnaE gene of *Synechocystis* sp. PCC6803", Proc. *Natl. Acad. Sci USA*, 95: 9226-9231 (1998).
Zettler, Jr., et al., "The naturallv split Npu DnaE intein exhibits an extraordinarily high rate in the protein trans-splicing reaction", *FEBS Letters*, 553: 909-914 (2009).

(56) References Cited

OTHER PUBLICATIONS

Molecular Probes Handbook, A Guide to Fluorescent Probes and Labeling Technologies, 11$^{th}$ Edition (2010), 26 pages.

Zhang, A., et al, "Construction of a mini-intein fusion system to allow both direct monitoring of soluble protein expression and rapid purification of target proteins" Gene, 275, 241-252 (2001).

Shah et al., "Inteins: Nature's Gift to Protein Chemists", Chemical Science, vol. 5, No. 1, Jan. 1, 2014, pp. 446-461.

"Gp41.8 Protein N-Terminal Split Intein, SEQ ID 12", retrieved from EBI accession No. GSP: BAM89814, May 23, 2013.

Chong et al., "Single-column purification of free recombinant proteins using a self-cleavable affinity tag derived from a protein splicing element", Gene, vol. 192, Issue 2, Jun. 19, 1997, pp. 271-281.

Cui et al., "Elimination of in vivo cleavage between target protein and intein in the intein-mediated protein purification systems", Protein Expression and Purification, vol. 50, Issue 1, Nov. 2006, pp. 74-81.

\* cited by examiner

SEQUENCE LISTING

<160> NUMBER OF SEQ ID NOS: 63

<210> SEQ ID NO 1
<211> LENGTH: 96
<212> TYPE: PRT
<213> ORGANISM: Artificial Sequence
<220> FEATURE:
<223> OTHER INFORMATION: GP41-1 N-intein with flanking non-intein
      sequences

<400> SEQUENCE: 1

Met Thr Arg Ser Gly Tyr Cys Leu Asp Leu Lys Thr Gln Val Gln Thr
1               5                   10                  15

Pro Gln Gly Met Lys Glu Ile Ser Asn Ile Gln Val Gly Asp Leu Val
            20                  25                  30

Leu Ser Asn Thr Gly Tyr Asn Glu Val Leu Asn Val Phe Pro Lys Ser
        35                  40                  45

Lys Lys Lys Ser Tyr Lys Ile Thr Leu Glu Asp Gly Lys Glu Ile Ile
    50                  55                  60

Cys Ser Glu Glu His Leu Phe Pro Thr Gln Thr Gly Glu Met Asn Ile
65                  70                  75                  80

Ser Gly Gly Leu Lys Glu Gly Met Cys Leu Tyr Val Lys Gly Gly
                85                  90                  95

<210> SEQ ID NO 2
<211> LENGTH: 96
<212> TYPE: PRT
<213> ORGANISM: Artificial Sequence
<220> FEATURE:
<223> OTHER INFORMATION: GP41-1 N-intein variant with flanking
      non-intein sequences

<400> SEQUENCE: 2

Met Thr Arg Ser Gly Tyr Ala Leu Asp Leu Lys Thr Gln Val Gln Thr
1               5                   10                  15

Pro Gln Gly Met Lys Glu Ile Ser Asn Ile Gln Val Gly Asp Leu Val
            20                  25                  30

Leu Ser Asn Thr Gly Tyr Asn Glu Val Leu Asn Val Phe Pro Lys Ser
        35                  40                  45

Lys Lys Lys Ser Tyr Lys Ile Thr Leu Glu Asp Gly Lys Glu Ile Ile
    50                  55                  60

Cys Ser Glu Glu His Leu Phe Pro Thr Gln Thr Gly Glu Met Asn Ile
65                  70                  75                  80

Ser Gly Gly Leu Lys Glu Gly Met Cys Leu Tyr Val Lys Gly Gly
                85                  90                  95

<210> SEQ ID NO 3
<211> LENGTH: 96
<212> TYPE: PRT
<213> ORGANISM: Artificial Sequence
<220> FEATURE:
<223> OTHER INFORMATION: GP41-1 N-intein variant with flanking
      non-intein sequences

<400> SEQUENCE: 3

Met Thr Arg Ser Gly Tyr Ala Leu Asp Leu Lys Thr Gln Val Gln Thr
1               5                   10                  15

Pro Gln Gly Met Lys Glu Ile Ser Asn Ile Gln Val Gly Asp Leu Val
            20                  25                  30

Leu Ser Asn Thr Gly Tyr Asn Glu Val Leu Asn Val Phe Pro Lys Ser
        35                  40                  45

```
Lys Lys Lys Ser Tyr Lys Ile Thr Leu Glu Asp Gly Lys Glu Ile Ile
        50                  55                  60

Ala Ser Glu Glu His Leu Phe Pro Thr Gln Thr Gly Glu Met Asn Ile
65                  70                  75                  80

Ser Gly Gly Leu Lys Glu Gly Met Cys Leu Tyr Val Lys Glu Gly Gly
            85                  90                  95
```

<210> SEQ ID NO 4
<211> LENGTH: 96
<212> TYPE: PRT
<213> ORGANISM: Artificial Sequence
<220> FEATURE:
<223> OTHER INFORMATION: GP41-1 N-intein variant with flanking
      non-intein sequences

<400> SEQUENCE: 4

```
Met Thr Arg Ser Gly Tyr Ala Leu Asp Leu Lys Thr Gln Val Gln Thr
1               5                   10                  15

Pro Gln Gly Met Lys Glu Ile Ser Asn Ile Gln Val Gly Asp Leu Val
            20                  25                  30

Leu Ser Asn Thr Gly Tyr Asn Glu Val Leu Asn Val Phe Pro Lys Ser
        35                  40                  45

Lys Lys Lys Ser Tyr Lys Ile Thr Leu Glu Asp Gly Lys Glu Ile Ile
        50                  55                  60

Cys Ser Glu Glu His Leu Phe Pro Thr Gln Thr Gly Glu Met Asn Ile
65                  70                  75                  80

Ser Gly Gly Leu Lys Glu Gly Met Lys Leu Tyr Val Lys Glu Gly Gly
            85                  90                  95
```

<210> SEQ ID NO 5
<211> LENGTH: 96
<212> TYPE: PRT
<213> ORGANISM: Artificial Sequence
<220> FEATURE:
<223> OTHER INFORMATION: GP41-1 N-intein variant with flanking
      non-intein sequences

<400> SEQUENCE: 5

```
Met Thr Arg Ser Gly Tyr Ala Leu Asp Leu Lys Thr Gln Val Gln Thr
1               5                   10                  15

Pro Gln Gly Met Lys Glu Ile Ser Asn Ile Gln Val Gly Asp Leu Val
            20                  25                  30

Leu Ser Asn Thr Gly Tyr Asn Glu Val Leu Asn Val Phe Pro Lys Ser
        35                  40                  45

Lys Lys Lys Ser Tyr Lys Ile Thr Leu Glu Asp Gly Lys Glu Ile Ile
        50                  55                  60

Ala Ser Glu Glu His Leu Phe Pro Thr Gln Thr Gly Glu Met Asn Ile
65                  70                  75                  80

Ser Gly Gly Leu Lys Glu Gly Met Met Leu Tyr Val Lys Glu Gly Gly
            85                  90                  95
```

<210> SEQ ID NO 6
<211> LENGTH: 96
<212> TYPE: PRT
<213> ORGANISM: Artificial Sequence
<220> FEATURE:
<223> OTHER INFORMATION: GP41-1 N-intein variant with flanking
      non-intein sequences

<400> SEQUENCE: 6

```
Met Thr Arg Ser Gly Tyr Ala Leu Asp Leu Lys Thr Gln Val Gln Thr
1               5                   10                  15

Pro Gln Gly Met Lys Glu Ile Ser Asn Ile Gln Val Gly Asp Leu Val
                20                  25                  30

Leu Ser Asn Thr Gly Tyr Asn Glu Val Leu Asn Val Phe Pro Lys Ser
            35                  40                  45

Lys Lys Lys Ser Tyr Lys Ile Thr Leu Glu Asp Gly Lys Glu Ile Ile
        50                  55                  60

Thr Ser Glu Glu His Leu Phe Pro Thr Gln Thr Gly Glu Met Asn Ile
65                  70                  75                  80

Ser Gly Gly Leu Lys Glu Gly Met Met Leu Tyr Val Lys Glu Gly Gly
                85                  90                  95
```

<210> SEQ ID NO 7
<211> LENGTH: 96
<212> TYPE: PRT
<213> ORGANISM: Artificial Sequence
<220> FEATURE:
<223> OTHER INFORMATION: GP41-1 N-intein variant with flanking
      non-intein sequences

<400> SEQUENCE: 7

```
Met Thr Arg Ser Gly Tyr Ala Leu Asp Leu Lys Thr Gln Val Gln Thr
1               5                   10                  15

Pro Gln Gly Met Lys Glu Ile Ser Asn Ile Gln Val Gly Asp Leu Val
                20                  25                  30

Leu Ser Asn Thr Gly Tyr Asn Glu Val Leu Asn Val Phe Pro Lys Ser
            35                  40                  45

Lys Lys Lys Ser Tyr Lys Ile Thr Leu Glu Asp Gly Lys Glu Ile Ile
        50                  55                  60

Ala Ser Glu Glu His Leu Phe Pro Thr Gln Thr Gly Glu Met Asn Ile
65                  70                  75                  80

Ser Gly Gly Leu Lys Glu Gly Met Lys Leu Tyr Val Lys Glu Gly Gly
                85                  90                  95
```

<210> SEQ ID NO 8
<211> LENGTH: 96
<212> TYPE: PRT
<213> ORGANISM: Artificial Sequence
<220> FEATURE:
<223> OTHER INFORMATION: GP41-1 N-intein variant with flanking
      non-intein sequences

<400> SEQUENCE: 8

```
Met Thr Arg Ser Gly Tyr Ala Leu Asp Leu Lys Thr Gln Val Gln Thr
1               5                   10                  15

Pro Gln Gly Met Lys Glu Ile Ser Asn Ile Gln Val Gly Asp Leu Val
                20                  25                  30

Leu Ser Asn Thr Gly Tyr Asn Glu Val Leu Asn Val Phe Pro Lys Ser
            35                  40                  45

Lys Lys Lys Ser Tyr Lys Ile Thr Leu Glu Asp Gly Lys Glu Ile Ile
        50                  55                  60

Thr Ser Glu Glu His Leu Phe Pro Thr Gln Thr Gly Glu Met Asn Ile
65                  70                  75                  80

Ser Gly Gly Leu Lys Glu Gly Met Lys Leu Tyr Val Lys Glu Gly Gly
                85                  90                  95
```

<210> SEQ ID NO 9
<211> LENGTH: 42

<212> TYPE: PRT
<213> ORGANISM: cyanophage

<400> SEQUENCE: 9

Met Gly Lys Asn Ser Met Met Leu Lys Lys Ile Leu Lys Ile Glu Glu
1               5                   10                  15

Leu Asp Glu Arg Glu Leu Ile Asp Ile Glu Val Ser Gly Asn His Leu
            20                  25                  30

Phe Tyr Ala Asn Asp Ile Leu Thr His Asn
        35                  40

<210> SEQ ID NO 10
<211> LENGTH: 157
<212> TYPE: PRT
<213> ORGANISM: Artificial Sequence
<220> FEATURE:
<223> OTHER INFORMATION: GP41-1 C-intein-thioredoxin fusion protein

<400> SEQUENCE: 10

Met Gly Lys Asn Ser Met Met Leu Lys Lys Ile Leu Lys Ile Glu Glu
1               5                   10                  15

Leu Asp Glu Arg Glu Leu Ile Asp Ile Glu Val Ser Gly Asn His Leu
            20                  25                  30

Phe Tyr Ala Asn Asp Ile Leu Thr His Asn Met Ser Asp Lys Ile Ile
        35                  40                  45

His Leu Thr Asp Asp Ser Phe Asp Thr Asp Val Leu Lys Ala Asp Gly
    50                  55                  60

Ala Ile Leu Val Asp Phe Trp Ala Glu Trp Cys Gly Pro Cys Lys Met
65                  70                  75                  80

Ile Ala Pro Ile Leu Asp Glu Ile Ala Asp Glu Tyr Gln Gly Lys Leu
                85                  90                  95

Thr Val Ala Lys Leu Asn Ile Asp Gln Asn Pro Gly Thr Ala Pro Lys
            100                 105                 110

Tyr Gly Ile Arg Gly Ile Pro Thr Leu Leu Leu Phe Lys Asn Gly Glu
        115                 120                 125

Val Ala Ala Thr Lys Val Gly Ala Leu Ser Lys Gly Gln Leu Lys Glu
    130                 135                 140

Phe Leu Asp Ala Asn Leu Ala His His His His His His
145                 150                 155

<210> SEQ ID NO 11
<211> LENGTH: 51
<212> TYPE: PRT
<213> ORGANISM: E. coli

<400> SEQUENCE: 11

Met Arg Glu Tyr Pro Asn Gly Glu Lys Thr His Leu Thr Val Met Ala
1               5                   10                  15

Ala Gly Phe Pro Ser Leu Thr Gly Asp His Lys Val Ile Tyr Val Ala
            20                  25                  30

Ala Asp Arg His Val Thr Ser Glu Glu Ile Leu Glu Ala Ala Ile Arg
        35                  40                  45

Leu Leu Ser
    50

<210> SEQ ID NO 12
<211> LENGTH: 77
<212> TYPE: PRT
<213> ORGANISM: E. coli

<400> SEQUENCE: 12

Met Ser His Leu Asp Glu Val Ile Ala Arg Val Asp Ala Ala Ile Glu
1               5                   10                  15

Glu Ser Val Ile Ala His Met Asn Glu Leu Leu Ile Ala Leu Ser Asp
                20                  25                  30

Asp Ala Glu Leu Ser Arg Glu Asp Arg Tyr Thr Gln Gln Gln Arg Leu
            35                  40                  45

Arg Thr Ala Ile Ala His His Gly Arg Lys His Lys Glu Asp Met Glu
50                  55                  60

Ala Arg His Glu Gln Leu Thr Lys Gly Gly Thr Ile Leu
65                  70                  75

<210> SEQ ID NO 13
<211> LENGTH: 83
<212> TYPE: PRT
<213> ORGANISM: E. coli

<400> SEQUENCE: 13

Met Asn Lys Glu Thr Gln Pro Ile Asp Arg Glu Thr Leu Leu Lys Glu
1               5                   10                  15

Ala Asn Lys Ile Ile Arg Glu His Glu Asp Thr Leu Ala Gly Ile Glu
                20                  25                  30

Ala Thr Gly Val Thr Gln Arg Asn Gly Val Leu Val Phe Thr Gly Asp
            35                  40                  45

Tyr Phe Leu Asp Glu Gln Gly Leu Pro Thr Ala Lys Ser Thr Ala Val
50                  55                  60

Phe Asn Met Phe Lys His Leu Ala His Val Leu Ser Glu Lys Tyr His
65                  70                  75                  80

Leu Val Asp

<210> SEQ ID NO 14
<211> LENGTH: 53
<212> TYPE: PRT
<213> ORGANISM: E. coli

<400> SEQUENCE: 14

Met Ser Leu Glu Asn Ala Pro Asp Asp Val Lys Leu Ala Val Asp Leu
1               5                   10                  15

Ile Val Leu Leu Glu Glu Asn Gln Ile Pro Ala Ser Thr Val Leu Arg
                20                  25                  30

Ala Leu Asp Ile Val Lys Arg Asp Tyr Glu Lys Lys Leu Thr Arg Asp
            35                  40                  45

Asp Glu Ala Glu Lys
    50

<210> SEQ ID NO 15
<211> LENGTH: 69
<212> TYPE: PRT
<213> ORGANISM: E. coli

<400> SEQUENCE: 15

Met Asn Lys Asp Glu Ala Gly Gly Asn Trp Lys Gln Phe Lys Gly Lys
1               5                   10                  15

Val Lys Glu Gln Trp Gly Lys Leu Thr Asp Asp Met Thr Ile Ile
                20                  25                  30

Glu Gly Lys Arg Asp Gln Leu Val Gly Lys Ile Gln Glu Arg Tyr Gly
            35                  40                  45

Tyr Gln Lys Asp Gln Ala Glu Lys Glu Val Val Asp Trp Glu Thr Arg
            50                  55                  60

Asn Glu Tyr Arg Trp
 65

<210> SEQ ID NO 16
<211> LENGTH: 70
<212> TYPE: PRT
<213> ORGANISM: E. coli

<400> SEQUENCE: 16

Met Asn Lys Asp Glu Ala Gly Gly Asn Trp Lys Gln Phe Lys Gly Lys
  1               5                  10                  15

Val Lys Glu Gln Trp Gly Cys Lys Leu Thr Asp Asp Met Thr Ile
             20                  25                  30

Ile Glu Gly Lys Arg Asp Gln Leu Val Gly Lys Ile Gln Glu Arg Tyr
             35                  40                  45

Gly Tyr Gln Lys Asp Gln Ala Glu Lys Glu Val Val Asp Trp Glu Thr
            50                  55                  60

Arg Asn Glu Tyr Arg Trp
 65                  70

<210> SEQ ID NO 17
<211> LENGTH: 70
<212> TYPE: PRT
<213> ORGANISM: E. coli

<400> SEQUENCE: 17

Met Asn Lys Asp Glu Ala Gly Gly Asn Trp Lys Gln Phe Lys Gly Lys
  1               5                  10                  15

Val Lys Glu Gln Trp Gly Lys Leu Thr Asp Asp Met Thr Ile Ile
             20                  25                  30

Glu Gly Lys Arg Asp Gln Leu Val Gly Lys Ile Gln Glu Arg Tyr Gly
             35                  40                  45

Cys Tyr Gln Lys Asp Gln Ala Glu Lys Glu Val Val Asp Trp Glu Thr
            50                  55                  60

Arg Asn Glu Tyr Arg Trp
 65                  70

<210> SEQ ID NO 18
<211> LENGTH: 71
<212> TYPE: PRT
<213> ORGANISM: E. coli

<400> SEQUENCE: 18

Met Asn Lys Asp Glu Ala Gly Gly Asn Trp Lys Gln Phe Lys Gly Lys
  1               5                  10                  15

Val Lys Glu Gln Trp Gly Lys Leu Thr Asp Asp Met Thr Ile Ile
             20                  25                  30

Glu Gly Lys Arg Asp Gln Leu Val Gly Lys Ile Gln Glu Arg Tyr Gly
             35                  40                  45

Cys Gly Tyr Gln Lys Asp Gln Ala Glu Lys Glu Val Val Asp Trp Glu
            50                  55                  60

Thr Arg Asn Glu Tyr Arg Trp
 65                  70

<210> SEQ ID NO 19
<211> LENGTH: 92

<212> TYPE: PRT
<213> ORGANISM: E. coli

<400> SEQUENCE: 19

Met Ile Ala Glu Phe Glu Ser Arg Ile Leu Ala Leu Ile Asp Gly Met
1               5                   10                  15

Val Asp His Ala Ser Asp Asp Glu Leu Phe Ala Ser Gly Tyr Leu Arg
            20                  25                  30

Gly His Leu Thr Leu Ala Ile Ala Glu Leu Glu Ser Gly Asp Asp His
        35                  40                  45

Ser Ala Gln Ala Val His Thr Thr Val Ser Gln Ser Leu Glu Lys Ala
    50                  55                  60

Ile Gly Ala Gly Glu Leu Ser Pro Arg Asp Gln Ala Leu Val Thr Asp
65                  70                  75                  80

Met Trp Glu Asn Leu Phe Gln Gln Ala Ser Gln Gln
                85                  90

<210> SEQ ID NO 20
<211> LENGTH: 95
<212> TYPE: PRT
<213> ORGANISM: E. coli

<400> SEQUENCE: 20

Met Gln Leu Asn Ile Thr Gly Asn Asn Val Glu Ile Thr Glu Ala Leu
1               5                   10                  15

Arg Glu Phe Val Thr Ala Lys Phe Ala Lys Leu Glu Gln Tyr Phe Asp
            20                  25                  30

Arg Ile Asn Gln Val Tyr Val Val Leu Lys Val Glu Lys Val Thr His
        35                  40                  45

Thr Ser Asp Ala Thr Leu His Val Asn Gly Gly Glu Ile His Ala Ser
    50                  55                  60

Ala Glu Gly Gln Asp Met Tyr Ala Ala Ile Asp Gly Leu Ile Asp Lys
65                  70                  75                  80

Leu Ala Arg Gln Leu Thr Lys His Lys Asp Lys Leu Lys Gln His
                85                  90                  95

<210> SEQ ID NO 21
<211> LENGTH: 192
<212> TYPE: PRT
<213> ORGANISM: E. coli

<400> SEQUENCE: 21

Met Asp Thr Ser Asn Ala Thr Ser Val Val Asn Val Ser Ala Ser Ser
1               5                   10                  15

Ser Thr Ser Thr Ile Tyr Asp Leu Gly Asn Met Ser Lys Asp Glu Val
            20                  25                  30

Val Lys Leu Phe Glu Glu Leu Gly Val Phe Gln Ala Ala Ile Leu Met
        35                  40                  45

Phe Ser Tyr Met Tyr Gln Ala Gln Ser Asn Leu Ser Ile Ala Lys Phe
    50                  55                  60

Ala Asp Met Asn Glu Ala Ser Lys Ala Ser Thr Thr Ala Gln Lys Met
65                  70                  75                  80

Ala Asn Leu Val Asp Ala Lys Ile Ala Asp Val Gln Ser Ser Thr Asp
                85                  90                  95

Lys Asn Ala Lys Ala Lys Leu Pro Gln Asp Val Ile Asp Tyr Ile Asn
                100                 105                 110

Asp Pro Arg Asn Asp Ile Ser Val Thr Gly Ile Ser Asp Leu Ser Gly

```
                    115                 120                 125

Asp Leu Ser Ala Gly Asp Leu Gln Thr Val Lys Ala Ala Ile Ser Ala
            130                 135                 140

Lys Ala Asn Asn Leu Thr Thr Val Val Asn Asn Ser Gln Leu Glu Ile
145                 150                 155                 160

Gln Gln Met Ser Asn Thr Leu Asn Leu Leu Thr Ser Ala Arg Ser Asp
                165                 170                 175

Val Gln Ser Leu Gln Tyr Arg Thr Ile Ser Ala Ile Ser Leu Gly Lys
            180                 185                 190

<210> SEQ ID NO 22
<211> LENGTH: 68
<212> TYPE: PRT
<213> ORGANISM: Fasciola hepatica

<400> SEQUENCE: 22

Met Pro Ser Val Glu Val Glu Lys Leu Leu His Val Leu Asp Arg Asn
1               5                   10                  15

Gly Asp Gly Lys Val Ser Ala Glu Glu Leu Lys Ala Phe Ala Asp Asp
            20                  25                  30

Ser Lys Tyr Pro Leu Asp Ser Asn Lys Ile Lys Ala Phe Ile Lys Glu
        35                  40                  45

His Asp Lys Asn Lys Asp Gly Lys Leu Asp Leu Lys Glu Leu Val Ser
    50                  55                  60

Ile Leu Ser Ser
65

<210> SEQ ID NO 23
<211> LENGTH: 11
<212> TYPE: PRT
<213> ORGANISM: Fasciola hepatica

<400> SEQUENCE: 23

Met Pro Ser Val Glu Val Glu Lys Leu Leu His
1               5                   10

<210> SEQ ID NO 24
<211> LENGTH: 328
<212> TYPE: PRT
<213> ORGANISM: E. coli

<400> SEQUENCE: 24

Met Gly Gln Leu Ile Asp Gly Val Trp His Asp Thr Trp Tyr Asp Thr
1               5                   10                  15

Lys Ser Thr Gly Gly Lys Phe Gln Arg Ser Ala Ser Ala Phe Arg Asn
            20                  25                  30

Trp Leu Thr Ala Asp Gly Ala Pro Gly Pro Thr Gly Lys Gly Gly Phe
        35                  40                  45

Ala Ala Glu Lys Asp Arg Tyr His Leu Tyr Val Ser Leu Ala Cys Pro
    50                  55                  60

Trp Ala His Arg Thr Leu Ile Met Arg Lys Leu Lys Gly Leu Glu Pro
65                  70                  75                  80

Phe Ile Ser Val Ser Val Val Asn Pro Leu Met Leu Glu Asn Gly Trp
                85                  90                  95

Thr Phe Asp Asp Ser Phe Pro Gly Ala Thr Gly Asp Thr Leu Tyr Gln
            100                 105                 110

His Glu Phe Leu Tyr Gln Leu Tyr Leu His Ala Asp Pro His Tyr Ser
        115                 120                 125
```

```
Gly Arg Val Thr Val Pro Val Leu Trp Asp Lys Lys Asn His Thr Ile
            130                 135                 140
Val Ser Asn Glu Ser Ala Glu Ile Ile Arg Met Phe Asn Thr Ala Phe
145                 150                 155                 160
Asp Ala Leu Gly Ala Lys Ala Gly Asp Tyr Tyr Pro Ala Leu Gln
                165                 170                 175
Pro Lys Ile Asp Glu Leu Asn Gly Trp Ile Tyr Asp Thr Val Asn Asn
                180                 185                 190
Gly Val Tyr Lys Ala Gly Phe Ala Thr Ser Gln Gln Ala Tyr Asp Glu
                195                 200                 205
Ala Val Ala Lys Val Phe Glu Ser Leu Ala Arg Leu Glu Gln Ile Leu
    210                 215                 220
Gly Gln His Arg Tyr Leu Thr Gly Asn Gln Leu Thr Glu Ala Asp Ile
225                 230                 235                 240
Arg Leu Trp Thr Thr Leu Val Arg Phe Asp Pro Val Tyr Val Thr His
                245                 250                 255
Phe Lys Cys Asp Lys His Arg Ile Ser Asp Tyr Leu Asn Leu Tyr Gly
                260                 265                 270
Phe Leu Arg Asp Ile Tyr Gln Met Pro Gly Ile Ala Glu Thr Val Asn
                275                 280                 285
Phe Asp His Ile Arg Asn His Tyr Phe Arg Ser His Lys Thr Ile Asn
                290                 295                 300
Pro Thr Gly Ile Ile Ser Ile Gly Pro Trp Gln Asp Leu Asp Glu Pro
305                 310                 315                 320
His Gly Arg Asp Val Arg Phe Gly
                325

<210> SEQ ID NO 25
<211> LENGTH: 120
<212> TYPE: PRT
<213> ORGANISM: Enterobacteria phage lambda

<400> SEQUENCE: 25

Met Ala Ser Trp Ser His Pro Gln Phe Glu Lys Ala Ser Lys Glu Thr
1               5                   10                  15
Phe Thr His Tyr Gln Pro Gln Gly Asn Ser Asp Pro Ala His Thr Ala
                20                  25                  30
Thr Ala Pro Gly Gly Leu Ser Ala Lys Ala Pro Ala Met Thr Pro Leu
            35                  40                  45
Met Leu Asp Thr Ser Ser Arg Lys Leu Val Ala Trp Asp Gly Thr Thr
50                  55                  60
Asp Gly Ala Ala Val Gly Ile Leu Ala Val Ala Asp Gln Thr Ser
65                  70                  75                  80
Thr Thr Leu Thr Phe Tyr Lys Ser Gly Thr Phe Arg Tyr Glu Asp Val
                85                  90                  95
Leu Trp Pro Glu Ala Ala Ser Asp Glu Thr Lys Lys Arg Thr Ala Phe
                100                 105                 110
Ala Gly Thr Ala Ile Ser Ile Val
        115                 120

<210> SEQ ID NO 26
<211> LENGTH: 396
<212> TYPE: PRT
<213> ORGANISM: E. coli

<400> SEQUENCE: 26
```

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
            85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
            115                 120                 125

Leu Ile Ala Tyr Pro Ile Ala Val Glu Ala Leu Ser Leu Ile Tyr Asn
            130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
            165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
            195                 200                 205

Val Asp Asn Ala Gly Ala Lys Ala Gly Leu Thr Phe Leu Val Asp Leu
210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
            275                 280                 285

Ser Ala Gly Ile Asn Ala Ala Ser Pro Asn Lys Glu Leu Ala Lys Glu
            290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
            355                 360                 365

Val Arg Thr Ala Val Ile Asn Ala Ala Ser Gly Arg Gln Thr Val Asp
370                 375                 380

Glu Ala Leu Lys Asp Ala Gln Thr Arg Ile Thr Lys
385                 390                 395

<210> SEQ ID NO 27
<211> LENGTH: 109
```

```
<212> TYPE: PRT
<213> ORGANISM: E. coli

<400> SEQUENCE: 27

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
                35                  40                  45

Glu Tyr Gln Gly Lys Leu Thr Val Ala Lys Leu Asn Ile Asp Gln Asn
            50                  55                  60

Pro Gly Thr Ala Pro Lys Tyr Gly Ile Arg Gly Ile Pro Thr Leu Leu
65              70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 28
<211> LENGTH: 495
<212> TYPE: PRT
<213> ORGANISM: E. coli

<400> SEQUENCE: 28

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
                20                  25                  30

Thr Ala Thr Lys Lys Lys Tyr Glu Gln Glu Ile Asp Val Arg Val Gln
            35                  40                  45

Ile Asp Arg Lys Ser Gly Asp Phe Asp Thr Phe Arg Arg Trp Leu Val
            50                  55                  60

Val Asp Glu Val Thr Gln Pro Thr Lys Glu Ile Thr Leu Glu Ala Ala
65              70                  75                  80

Arg Tyr Glu Asp Glu Ser Leu Asn Leu Gly Asp Tyr Val Glu Asp Gln
                85                  90                  95

Ile Glu Ser Val Thr Phe Asp Arg Ile Thr Thr Gln Thr Ala Lys Gln
                100                 105                 110

Val Ile Val Gln Lys Val Arg Glu Ala Glu Arg Ala Met Val Val Asp
            115                 120                 125

Gln Phe Arg Glu His Glu Gly Glu Ile Ile Thr Gly Val Val Lys Lys
        130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
            180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
    210                 215                 220

Ala Ala Ala Arg Asp Pro Gly Ser Arg Ala Lys Ile Ala Val Lys Thr
225                 230                 235                 240
```

```
Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
            260                 265                 270

Ile Val Leu Trp Asp Asp Asn Pro Ala Gln Phe Val Ile Asn Ala Met
        275                 280                 285

Ala Pro Ala Asp Val Ala Ser Ile Val Val Asp Glu Asp Lys His Thr
    290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
            340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
    370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Gly Val Asp Arg Asp Leu Ala Phe Lys Leu
        435                 440                 445

Ala Ala Arg Gly Val Cys Thr Leu Glu Asp Leu Ala Glu Gln Gly Ile
450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala
                485                 490                 495

<210> SEQ ID NO 29
<211> LENGTH: 88
<212> TYPE: PRT
<213> ORGANISM: GP41-1 N-intein (cyanophage)

<400> SEQUENCE: 29

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Ser Tyr Lys
        35                  40                  45

Ile Thr Leu Glu Asp Gly Lys Glu Ile Ile Cys Ser Glu Glu His Leu
    50                  55                  60

Phe Pro Thr Gln Thr Gly Glu Met Asn Ile Ser Gly Gly Leu Lys Glu
65                  70                  75                  80

Gly Met Cys Leu Tyr Val Lys Glu
                85

<210> SEQ ID NO 30
<211> LENGTH: 88
<212> TYPE: PRT
<213> ORGANISM: Unknown
```

```
<220> FEATURE:
<223> OTHER INFORMATION: N-terminal domain of GP41.8

<400> SEQUENCE: 30

Cys Leu Ser Leu Asp Thr Met Val Val Thr Asn Gly Lys Ala Ile Glu
1               5                   10                  15

Ile Arg Asp Val Lys Val Gly Asp Trp Leu Glu Ser Glu Cys Gly Pro
            20                  25                  30

Val Gln Val Thr Glu Val Leu Pro Ile Ile Lys Gln Pro Val Phe Glu
        35                  40                  45

Ile Val Leu Lys Ser Gly Lys Lys Ile Arg Val Ser Ala Asn His Lys
    50                  55                  60

Phe Pro Thr Lys Asp Gly Leu Lys Thr Ile Asn Ser Gly Leu Lys Val
65                  70                  75                  80

Gly Asp Phe Leu Arg Ser Arg Ala
                85

<210> SEQ ID NO 31
<211> LENGTH: 105
<212> TYPE: PRT
<213> ORGANISM: Unknown
<220> FEATURE:
<223> OTHER INFORMATION: N-terminal domain of NrdJ1

<400> SEQUENCE: 31

Cys Leu Val Gly Ser Ser Glu Ile Ile Thr Arg Asn Tyr Gly Lys Thr
1               5                   10                  15

Thr Ile Lys Glu Val Val Glu Ile Phe Asp Asn Asp Lys Asn Ile Gln
            20                  25                  30

Val Leu Ala Phe Asn Thr His Thr Asp Asn Ile Glu Trp Ala Pro Ile
        35                  40                  45

Lys Ala Ala Gln Leu Thr Arg Pro Asn Ala Glu Leu Val Glu Leu Glu
    50                  55                  60

Ile Asn Thr Leu His Gly Val Lys Thr Ile Arg Cys Thr Pro Asp His
65                  70                  75                  80

Pro Val Tyr Thr Lys Asn Arg Asp Tyr Val Arg Ala Asp Glu Leu Thr
                85                  90                  95

Asp Asp Asp Glu Leu Val Val Ala Ile
            100                 105

<210> SEQ ID NO 32
<211> LENGTH: 101
<212> TYPE: PRT
<213> ORGANISM: Unknown
<220> FEATURE:
<223> OTHER INFORMATION: N-terminal domain of IMPDH1

<400> SEQUENCE: 32

Cys Phe Val Pro Gly Thr Leu Val Asn Thr Glu Asn Gly Leu Lys Lys
1               5                   10                  15

Ile Glu Glu Ile Lys Val Gly Asp Lys Val Phe Ser His Thr Gly Lys
            20                  25                  30

Leu Gln Glu Val Val Asp Thr Leu Ile Phe Asp Arg Asp Glu Glu Ile
        35                  40                  45

Ile Ser Ile Asn Gly Ile Asp Cys Thr Lys Asn His Glu Phe Tyr Val
    50                  55                  60

Ile Asp Lys Glu Asn Ala Asn Arg Val Asn Glu Asp Asn Ile His Leu
65                  70                  75                  80
```

```
Phe Ala Arg Trp Val His Ala Glu Glu Leu Asp Met Lys Lys His Leu
                85                  90                  95

Leu Ile Glu Leu Glu
            100

<210> SEQ ID NO 33
<211> LENGTH: 106
<212> TYPE: PRT
<213> ORGANISM: Unknown
<220> FEATURE:
<223> OTHER INFORMATION: N-terminal domain of NrdA-2

<400> SEQUENCE: 33

Cys Leu Thr Gly Asp Ala Lys Ile Asp Val Leu Ile Asp Asn Ile Pro
1               5                   10                  15

Ile Ser Gln Ile Ser Leu Glu Glu Val Val Asn Leu Phe Asn Glu Gly
            20                  25                  30

Lys Glu Ile Tyr Val Leu Ser Tyr Asn Ile Asp Thr Lys Glu Val Glu
        35                  40                  45

Tyr Lys Glu Ile Ser Asp Ala Gly Leu Ile Ser Glu Ser Ala Glu Val
    50                  55                  60

Leu Glu Ile Ile Asp Glu Glu Thr Gly Gln Lys Ile Val Cys Thr Pro
65                  70                  75                  80

Asp His Lys Val Tyr Thr Leu Asn Arg Gly Tyr Val Ser Ala Lys Asp
                85                  90                  95

Leu Lys Glu Asp Asp Glu Leu Val Phe Ser
            100                 105

<210> SEQ ID NO 34
<211> LENGTH: 102
<212> TYPE: PRT
<213> ORGANISM: Nostoc punctiforme

<400> SEQUENCE: 34

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Cys Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn
            100

<210> SEQ ID NO 35
<211> LENGTH: 105
<212> TYPE: PRT
<213> ORGANISM: Synechocystis

<400> SEQUENCE: 35

Cys Ile Ser Gly Asp Ser Leu Ile Ser Leu Ala Ser Thr Gly Lys Arg
1               5                   10                  15

Val Ser Ile Lys Asp Leu Leu Asp Glu Lys Asp Phe Glu Ile Trp Ala
            20                  25                  30
```

Ile Asn Glu Gln Thr Met Lys Leu Glu Ser Ala Lys Val Ser Arg Val
            35                  40                  45

Phe Cys Thr Gly Lys Lys Leu Val Tyr Ile Leu Lys Thr Arg Leu Gly
        50                  55                  60

Arg Thr Ile Lys Ala Thr Ala Asn His Arg Phe Leu Thr Ile Asp Gly
65                  70                  75                  80

Trp Lys Arg Leu Asp Glu Leu Ser Leu Lys Glu His Ile Ala Leu Pro
                85                  90                  95

Arg Lys Leu Glu Ser Ser Ser Leu Gln
            100                 105

<210> SEQ ID NO 36
<211> LENGTH: 45
<212> TYPE: PRT
<213> ORGANISM: Unknown
<220> FEATURE:
<223> OTHER INFORMATION: C-terminal domain of GP41.8

<400> SEQUENCE: 36

Met Cys Glu Ile Phe Glu Asn Glu Ile Asp Trp Asp Glu Ile Ala Ser
1               5                   10                  15

Ile Glu Tyr Val Gly Val Glu Gly Thr Ile Asp Ile Asn Val Thr Asn
            20                  25                  30

Asp Arg Leu Phe Phe Ala Asn Gly Ile Leu Thr His Asn
            35                  40                  45

<210> SEQ ID NO 37
<211> LENGTH: 40
<212> TYPE: PRT
<213> ORGANISM: Unknown
<220> FEATURE:
<223> OTHER INFORMATION: C-terminal domain of NrdJ1

<400> SEQUENCE: 37

Met Glu Ala Lys Thr Tyr Ile Gly Lys Leu Lys Ser Arg Lys Ile Val
1               5                   10                  15

Ser Asn Glu Asp Thr Tyr Asp Ile Gln Thr Ser Thr His Asn Phe Phe
            20                  25                  30

Ala Asn Asp Ile Leu Val His Asn
            35                  40

<210> SEQ ID NO 38
<211> LENGTH: 40
<212> TYPE: PRT
<213> ORGANISM: Unknown
<220> FEATURE:
<223> OTHER INFORMATION: C-terminal domain of IMPDH1

<400> SEQUENCE: 38

Met Lys Phe Lys Leu Lys Glu Ile Thr Ser Ile Glu Thr Lys His Tyr
1               5                   10                  15

Lys Gly Lys Val His Asp Leu Thr Val Asn Gln Asp His Ser Tyr Asn
            20                  25                  30

Val Arg Gly Thr Val Val His Asn
            35                  40

<210> SEQ ID NO 39
<211> LENGTH: 34
<212> TYPE: PRT
<213> ORGANISM: Unknown
<220> FEATURE:

<223> OTHER INFORMATION: C-terminal domain of NrdA-2

<400> SEQUENCE: 39

Met Gly Leu Lys Ile Ile Lys Arg Glu Ser Lys Glu Pro Val Phe Asp
1               5                   10                  15

Ile Thr Val Lys Asp Asn Ser Asn Phe Phe Ala Asn Asn Ile Leu Val
            20                  25                  30

His Asn

<210> SEQ ID NO 40
<211> LENGTH: 36
<212> TYPE: PRT
<213> ORGANISM: Nostoc punctiforme

<400> SEQUENCE: 40

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn
        35

<210> SEQ ID NO 41
<211> LENGTH: 48
<212> TYPE: PRT
<213> ORGANISM: Synechocystis

<400> SEQUENCE: 41

Ser Pro Glu Ile Glu Lys Leu Ser Gln Ser Asp Ile Tyr Trp Asp Ser
1               5                   10                  15

Ile Val Ser Ile Thr Glu Thr Gly Val Glu Glu Val Phe Asp Leu Thr
            20                  25                  30

Val Pro Gly Pro His Asn Phe Val Ala Asn Asp Ile Ile Val His Asn
        35                  40                  45

<210> SEQ ID NO 42
<211> LENGTH: 27
<212> TYPE: PRT
<213> ORGANISM: Unknown
<220> FEATURE:
<223> OTHER INFORMATION: GP41-2 N-intein sequence

<400> SEQUENCE: 42

Cys Leu Asp Leu Lys Thr Gln Val Gln Thr Gln Gln Gly Leu Lys Asp
1               5                   10                  15

Ile Ser Asn Ile Gln Val Gly Asp Leu Val Leu
            20                  25

<210> SEQ ID NO 43
<211> LENGTH: 46
<212> TYPE: PRT
<213> ORGANISM: Unknown
<220> FEATURE:
<223> OTHER INFORMATION: GP41-3 N-intein sequence

<400> SEQUENCE: 43

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Lys Ser

<210> SEQ ID NO 44
<211> LENGTH: 88
<212> TYPE: PRT
<213> ORGANISM: Unknown
<220> FEATURE:
<223> OTHER INFORMATION: GP41-4 N-intein sequence

<400> SEQUENCE: 44

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Lys Ser Tyr Lys
        35                  40                  45

Ile Thr Leu Glu Asp Gly Lys Glu Ile Ile Cys Ser Glu Glu His Leu
    50                  55                  60

Phe Pro Thr Gln Thr Gly Glu Met Asn Ile Ser Gly Gly Leu Lys Glu
65                  70                  75                  80

Gly Met Cys Leu Tyr Val Lys Glu
                85

<210> SEQ ID NO 45
<211> LENGTH: 88
<212> TYPE: PRT
<213> ORGANISM: Unknown
<220> FEATURE:
<223> OTHER INFORMATION: GP41-5 N-intein sequence

<400> SEQUENCE: 45

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Lys Ser Tyr Lys
        35                  40                  45

Ile Thr Leu Glu Asp Gly Lys Glu Ile Ile Cys Ser Glu Glu His Leu
    50                  55                  60

Phe Pro Thr Gln Thr Gly Glu Met Asn Ile Ser Gly Gly Leu Lys Glu
65                  70                  75                  80

Gly Met Cys Leu Tyr Val Lys Glu
                85

<210> SEQ ID NO 46
<211> LENGTH: 43
<212> TYPE: PRT
<213> ORGANISM: Unknown
<220> FEATURE:
<223> OTHER INFORMATION: GP41-6 N-intein sequence

<400> SEQUENCE: 46

Ser Tyr Lys Ile Thr Leu Glu Asp Gly Lys Glu Ile Ile Cys Ser Glu
1               5                   10                  15

Glu His Leu Phe Pro Thr Gln Asn Gly Glu Val Asn Ile Lys Gly Gly
            20                  25                  30

Leu Lys Glu Gly Met Cys Leu Tyr Val Lys Glu
        35                  40

<210> SEQ ID NO 47

```
<211> LENGTH: 26
<212> TYPE: PRT
<213> ORGANISM: Unknown
<220> FEATURE:
<223> OTHER INFORMATION: GP41-7 N-intein sequence

<400> SEQUENCE: 47

Met Met Leu Lys Lys Ile Leu Lys Ile Glu Glu Leu Asp Glu Arg Glu
1               5                   10                  15

Leu Ile Asp Ile Glu Val Ser Gly Asn His
            20                  25

<210> SEQ ID NO 48
<211> LENGTH: 133
<212> TYPE: PRT
<213> ORGANISM: Unknown
<220> FEATURE:
<223> OTHER INFORMATION: NrdA-1 N-intein sequence

<400> SEQUENCE: 48

Cys Val Ala Gly Asp Thr Lys Ile Lys Ile Lys Tyr Pro Glu Ser Val
1               5                   10                  15

Gly Asp Gln Tyr Gly Thr Trp Tyr Trp Asn Val Leu Glu Lys Glu Ile
            20                  25                  30

Gln Ile Glu Asp Leu Glu Asp Tyr Ile Ile Met Arg Glu Cys Glu Ile
        35                  40                  45

Tyr Asp Ser Asn Ala Pro Gln Ile Glu Val Leu Ser Tyr Asn Ile Glu
    50                  55                  60

Thr Gly Glu Gln Glu Trp Lys Pro Ile Thr Ala Phe Ala Gln Thr Ser
65                  70                  75                  80

Pro Lys Ala Lys Val Met Lys Ile Thr Asp Glu Glu Ser Gly Lys Ser
                85                  90                  95

Ile Val Val Thr Pro Glu His Gln Val Phe Thr Lys Asn Arg Gly Tyr
            100                 105                 110

Val Met Ala Lys Asp Leu Ile Glu Thr Asp Glu Pro Ile Ile Val Asn
        115                 120                 125

Lys Asp Met Asn Phe
    130

<210> SEQ ID NO 49
<211> LENGTH: 105
<212> TYPE: PRT
<213> ORGANISM: Unknown
<220> FEATURE:
<223> OTHER INFORMATION: NrdA-4 N-intein sequence

<400> SEQUENCE: 49

Cys Leu Ala Gly Asp Thr Thr Val Thr Val Leu Glu Gly Asp Ile Val
1               5                   10                  15

Phe Glu Met Thr Leu Glu Asn Leu Val Ser Leu Tyr Lys Asn Val Phe
            20                  25                  30

Ser Val Ser Val Leu Ser Phe Asn Pro Glu Thr Gln Lys Gln Glu Phe
        35                  40                  45

Lys Pro Val Thr Asn Ala Ala Leu Met Asn Pro Glu Ser Lys Val Leu
    50                  55                  60

Lys Ile Thr Asp Ser Asp Thr Gly Lys Ser Ile Val Cys Thr Pro Asp
65                  70                  75                  80

His Lys Val Phe Thr Lys Asn Arg Gly Tyr Val Ile Ala Ser Glu Leu
                85                  90                  95
```

```
Asn Ala Glu Asp Ile Leu Glu Ile Lys
            100                 105
```

<210> SEQ ID NO 50
<211> LENGTH: 65
<212> TYPE: PRT
<213> ORGANISM: Unknown
<220> FEATURE:
<223> OTHER INFORMATION: NrdA-5 N-intein sequence

<400> SEQUENCE: 50

```
His Thr Glu Thr Val Arg Arg Val Gly Thr Ile Thr Ala Phe Ala Gln
1               5                   10                  15

Thr Ser Pro Lys Ser Lys Val Met Lys Ile Thr Asp Glu Glu Ser Gly
            20                  25                  30

Asn Ser Ile Val Val Thr Pro Glu His Lys Val Phe Thr Lys Asn Arg
        35                  40                  45

Gly Tyr Val Met Ala Lys Asn Leu Val Glu Thr Asp Glu Leu Val Ile
    50                  55                  60

Asn
65
```

<210> SEQ ID NO 51
<211> LENGTH: 49
<212> TYPE: PRT
<213> ORGANISM: Unknown
<220> FEATURE:
<223> OTHER INFORMATION: NrdA-6 N-intein sequence

<400> SEQUENCE: 51

```
Tyr Val Cys Ser Arg Asp Asp Thr Thr Gly Phe Lys Leu Ile Cys Thr
1               5                   10                  15

Pro Asp His Met Ile Tyr Thr Lys Asn Arg Gly Tyr Ile Met Ala Lys
            20                  25                  30

Tyr Leu Lys Glu Asp Asp Glu Leu Leu Ile Asn Glu Ile His Leu Pro
        35                  40                  45

Thr
```

<210> SEQ ID NO 52
<211> LENGTH: 105
<212> TYPE: PRT
<213> ORGANISM: Unknown
<220> FEATURE:
<223> OTHER INFORMATION: NrdJ-1 N-intein sequence

<400> SEQUENCE: 52

```
Cys Leu Val Gly Ser Ser Glu Ile Ile Thr Arg Asn Tyr Gly Lys Thr
1               5                   10                  15

Thr Ile Lys Glu Val Val Glu Ile Phe Asp Asn Asp Lys Asn Ile Gln
            20                  25                  30

Val Leu Ala Phe Asn Thr His Thr Asp Asn Ile Glu Trp Ala Pro Ile
        35                  40                  45

Lys Ala Ala Gln Leu Thr Arg Pro Asn Ala Glu Leu Val Glu Leu Glu
    50                  55                  60

Ile Asp Thr Leu His Gly Val Lys Thr Ile Arg Cys Thr Pro Asp His
65                  70                  75                  80

Pro Val Tyr Thr Lys Asn Arg Gly Tyr Val Arg Ala Asp Glu Leu Thr
                85                  90                  95

Asp Asp Asp Glu Leu Val Val Ala Ile
            100                 105
```

<210> SEQ ID NO 53
<211> LENGTH: 105
<212> TYPE: PRT
<213> ORGANISM: Unknown
<220> FEATURE:
<223> OTHER INFORMATION: NrdJ2 N-intein sequence

<400> SEQUENCE: 53

Cys Leu Val Gly Ser Ser Glu Ile Ile Thr Arg Asn Tyr Gly Lys Thr
1               5                   10                  15

Thr Ile Lys Glu Val Val Glu Ile Phe Asp Asn Asp Lys Asn Ile Gln
            20                  25                  30

Val Leu Ala Phe Asn Thr His Thr Asp Asn Ile Glu Trp Ala Pro Ile
        35                  40                  45

Lys Ala Ala Gln Leu Thr Arg Pro Asn Ala Glu Leu Val Glu Leu Glu
    50                  55                  60

Ile Asn Thr Leu His Gly Val Lys Thr Ile Arg Cys Thr Pro Asp His
65                  70                  75                  80

Pro Val Tyr Thr Lys Asn Arg Asp Tyr Val Arg Ala Asp Glu Leu Thr
                85                  90                  95

Asp Asp Asp Glu Leu Val Val Ala Ile
            100                 105

<210> SEQ ID NO 54
<211> LENGTH: 47
<212> TYPE: PRT
<213> ORGANISM: Unknown
<220> FEATURE:
<223> OTHER INFORMATION: GP41-9 C-intein sequence

<400> SEQUENCE: 54

Met Ile Met Lys Asn Arg Glu Arg Phe Ile Thr Glu Lys Ile Leu Asn
1               5                   10                  15

Ile Glu Glu Ile Asp Asp Asp Leu Thr Val Asp Ile Gly Met Asp Asn
            20                  25                  30

Glu Asp His Tyr Phe Val Ala Asn Asp Ile Leu Thr His Asn Thr
        35                  40                  45

<210> SEQ ID NO 55
<211> LENGTH: 42
<212> TYPE: PRT
<213> ORGANISM: Unknown
<220> FEATURE:
<223> OTHER INFORMATION: IMPDH-2 C-intein sequence

<400> SEQUENCE: 55

Met Lys Phe Thr Leu Glu Pro Ile Thr Lys Ile Asp Ser Tyr Glu Val
1               5                   10                  15

Thr Ala Glu Pro Val Tyr Asp Ile Glu Val Glu Asn Asp His Ser Phe
            20                  25                  30

Cys Val Asn Gly Phe Val Val His Asn Ser
        35                  40

<210> SEQ ID NO 56
<211> LENGTH: 41
<212> TYPE: PRT
<213> ORGANISM: Unknown
<220> FEATURE:
<223> OTHER INFORMATION: IMPDH-3 C-intein sequence

<400> SEQUENCE: 56

Met Lys Phe Lys Leu Val Glu Ile Thr Ser Lys Glu Thr Phe Asn Tyr
1               5                   10                  15

Ser Gly Gln Val His Asp Leu Thr Val Glu Asp Asp His Ser Tyr Ser
                20                  25                  30

Ile Asn Asn Ile Val Val His Asn Ser
        35                  40

<210> SEQ ID NO 57
<211> LENGTH: 34
<212> TYPE: PRT
<213> ORGANISM: Unknown
<220> FEATURE:
<223> OTHER INFORMATION: NrdA-3 C-intein sequence

<400> SEQUENCE: 57

Met Leu Lys Ile Glu Tyr Leu Glu Glu Ile Pro Val Tyr Asp Ile
1               5                   10                  15

Thr Val Glu Glu Thr His Asn Phe Phe Ala Asn Asp Ile Leu Ile His
                20                  25                  30

Asn Cys

<210> SEQ ID NO 58
<211> LENGTH: 28
<212> TYPE: PRT
<213> ORGANISM: Unknown
<220> FEATURE:
<223> OTHER INFORMATION: NrdA-5 C-intein sequence

<400> SEQUENCE: 58

Met Leu Lys Ile Glu Tyr Leu Glu Glu Ile Pro Val Tyr Asp Ile
1               5                   10                  15

Thr Val Glu Gly Thr His Asn Leu Ala Tyr Ser Leu
                20                  25

<210> SEQ ID NO 59
<211> LENGTH: 33
<212> TYPE: PRT
<213> ORGANISM: Unknown
<220> FEATURE:
<223> OTHER INFORMATION: NrdA-6 C-intein sequence

<400> SEQUENCE: 59

Met Gly Ile Lys Ile Arg Lys Leu Glu Gln Asn Arg Val Tyr Asp Ile
1               5                   10                  15

Lys Val Glu Lys Ile Ile Phe Cys Asn Asn Ile Leu Val His Asn
                20                  25                  30

Cys

<210> SEQ ID NO 60
<211> LENGTH: 41
<212> TYPE: PRT
<213> ORGANISM: Unknown
<220> FEATURE:
<223> OTHER INFORMATION: NrdJ-1 C-intein sequence

<400> SEQUENCE: 60

Met Glu Ala Lys Thr Tyr Ile Gly Lys Leu Lys Ser Arg Lys Ile Val
1               5                   10                  15

Ser Asn Glu Asp Thr Tyr Asp Ile Gln Thr Ser Thr His Asn Phe Phe
                20                  25                  30

Ala Asn Asp Ile Leu Val His Asn Ser

```
<210> SEQ ID NO 61
<211> LENGTH: 4
<212> TYPE: PRT
<213> ORGANISM: Artificial Sequence
<220> FEATURE:
<223> OTHER INFORMATION: Loop region of E. coli

<400> SEQUENCE: 61

Gly Cys Lys Leu
1

<210> SEQ ID NO 62
<211> LENGTH: 4
<212> TYPE: PRT
<213> ORGANISM: Artificial Sequence
<220> FEATURE:
<223> OTHER INFORMATION: Loop region of E. coli

<400> SEQUENCE: 62

Gly Cys Tyr Gln
1

<210> SEQ ID NO 63
<211> LENGTH: 5
<212> TYPE: PRT
<213> ORGANISM: Artificial Sequence
<220> FEATURE:
<223> OTHER INFORMATION: Loop region of E. coli

<400> SEQUENCE: 63

Gly Cys Gly Tyr Gln
1               5
```

US 11,326,154 B2

SOLUBLE INTEIN FUSION PROTEINS AND METHODS FOR PURIFYING BIOMOLECULES

RELATED APPLICATIONS

This application is a continuation of U.S. application Ser. No. 15/511,908, filed on Mar. 16, 2017 which is the U.S. National Stage of International Application No. PCT/US2015/057125, filed Oct. 23, 2015, which designates the U.S., published in English, and claims the benefit of U.S. Provisional Application No. 62/074,494, filed on Nov. 3, 2014, and U.S. Provisional Application No. 62/209,010, filed on Aug. 24, 2015. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 00462053028_SEQUENCELISTING.txt; created Apr. 16, 2019, 51 KB in size.

FIELD OF THE INVENTION

The present invention relates to fusion proteins comprising an N-intein polypeptide and an N-intein solubilization partner, affinity chromatography matrices comprising such fusion proteins, and methods of using such fusion proteins in protein purification and peptidic ligation processes, particularly at industrial scale.

BACKGROUND OF THE INVENTION

Protein purification methods that involve tagging a protein of interest with an affinity tag are widely used in laboratory settings for R&D applications, but have proven to be impractical for large-scale manufacturing operations. In the bioprocessing industry, only cleavable affinity tags are used to ensure that the final product does not contain the tag, which must be removed during production, typically using a site-specific protease. Removing the affinity tag requires additional process steps, which substantially increases cost and time, particularly at industrial scale. Moreover, inefficient and off-site cleavage leads to contamination of the final protein product with proteins that retain the tag and truncated protein fragments, respectively, which is not acceptable in bioprocessing applications.

Accordingly, there is a need to develop improved affinity chromatography reagents and methods that permit large-scale purification of proteins under industrial conditions.

SUMMARY OF THE INVENTION

Inteins are a class of autocatalytic enzymes that contain both protease and ligase activities. One class of inteins, termed "split inteins," involves two complementary half inteins, termed the N-intein and C-intein, that associate selectively and extremely tightly to form an active intein enzyme (Shah N. H., et al, *J. Amer. Chem. Soc.* 135: 18673-18681; Dassa B., et al., *Nucl. Acids Res.*, 37:2560-2573 (2009)).

The use of inteins, including split inteins, in large-scale protein purification processes has been previously described in the prior art (see, e.g., WO 2013/045632). The use of split inteins for the chromatographic separation of proteins of interest from crude mixtures has also been described previously (see, e.g., Chinese Publication No. CN101884910; Guan D., et al., *Biotech. Bioeng.* 110:2471-2481 (2013); Lu W., et al., *J. Chrom. A,* 1218: 2553-2560 (2011)).

However, the use of inteins in large-scale protein purification processes is hindered by their poor solubility when expressed in common expression systems, such as *E. Coli*. Furthermore, a chromatography matrix that includes an intein-based affinity ligand that is covalently attached to a solid support, which is critical for efficient industrial-scale protein purification processes, has not been described.

The present invention provides soluble fusion proteins comprising an N-intein polypeptide capable of forming an active intein complex by associating with a second fusion protein comprising a C-intein polypeptide. The fusion proteins comprising an N-intein polypeptide can be covalently attached to a solid support to produce an affinity chromatography matrix that is suitable for large-scale bioprocessing applications.

Accordingly, in one embodiment, the present invention relates to a fusion protein comprising an N-intein polypeptide and an N-intein solubilization partner joined by a peptide bond. In a particular aspect of this embodiment, the N-intein solubilization partner has a molecular weight of less than about 15 kDa, an Aliphatic Index value less than about 60, and a Grand Average Hydropathy value less than −1, and enhances (e.g., increases and/or promotes) solubility of the N-intein polypeptide. In a further aspect of this embodiment, the N-intein solubilization partner comprises SEQ ID NO:15. In yet another aspect of this embodiment, the N-intein polypeptide is the GP41-1 N-intein (SEQ ID NO:1), or a variant thereof.

In another embodiment, the invention relates to an affinity chromatography matrix comprising a fusion protein comprising an N-intein polypeptide and an N-intein solubilization partner, attached to a solid support. In a particular aspect of this embodiment, the solid support is a chromatography resin that includes a hydrophilic polyvinyl ether base.

In a further embodiment, the invention relates to a method of affinity purifying a target molecule in a sample. In one aspect of this embodiment, the method comprises a) providing a sample containing a first fusion protein comprising a C-intein polypeptide joined to a target molecule by a peptide bond; b) contacting the sample with an affinity chromatography matrix that comprises a second fusion protein, wherein the second fusion protein comprises an N-intein polypeptide joined by a peptide bond to an N-intein solubilization partner that promotes solubility of the N-intein polypeptide, under conditions in which the C-intein polypeptide in the first fusion protein selectively binds to the N-intein polypeptide in the second fusion protein to form an intein complex that is inactive; c) washing the affinity chromatography matrix containing the inactive intein complex to remove unbound contaminants; d) exposing the intein complex to conditions under which the intein complex is active and cleaves the target molecule from the C-intein polypeptide; and e) recovering the cleaved target molecule.

In yet another embodiment, the invention relates to a method of screening for a catalytically-active intein complex that is suitable for use in affinity purification. In an aspect of this embodiment, the method comprises a) contacting a first fusion protein that comprises a C-intein polypeptide joined to a target molecule (e.g., by a peptide bond or linker molecule) with a second fusion protein that comprises an N-intein polypeptide joined to an N-intein solubilization partner (e.g., by a peptide bond or linker molecule), under conditions in which the C-intein polypeptide in the first fusion protein selectively binds to the N-intein polypeptide in the second fusion protein to form an intein complex; and b) determining whether the target molecule is cleaved from the C-intein polypeptide under conditions which support intein activity, wherein the presence of the cleaved target molecule is indicative of a catalytically-active intein complex.

The N-intein fusion proteins of the present invention have improved solubility and enhanced catalytic activity, and are useful as reagents for performing large-scale protein purification (e.g., affinity chromatography) and modification processes (e.g., peptidic cleavage and ligation reactions) when partnered with the corresponding C-intein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows the various components before binding of the C-intein fusion protein to the N-intein affinity chromatography matrix. FIG. 1B shows the C-intein fusion protein bound to the N-intein affinity chromatography matrix under appropriate conditions (e.g., pH, salt, oxidation/reduction) for intein association. FIG. 1C shows the components after the N- and C-exteins have been cleaved from their respective fusion proteins under appropriate conditions for catalytic activity of the intein complex.

DETAILED DESCRIPTION OF THE INVENTION

Figure 1:
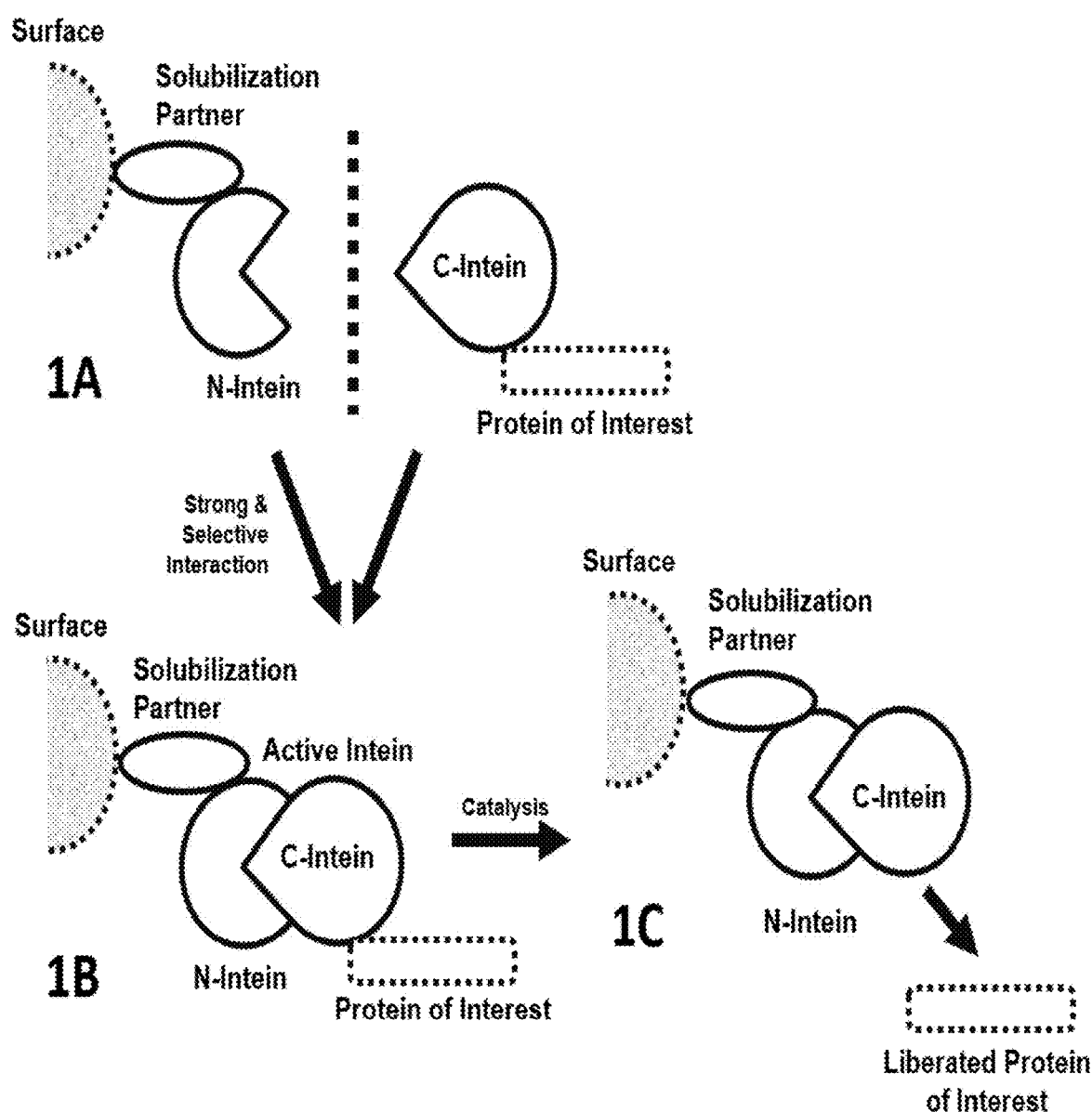
FIG. 1 is a schematic diagram depicting an exemplary affinity purification method of the invention. The method employs an exemplary affinity chromatography matrix of the invention comprising a fusion protein having an N-intein polypeptide fused to an N-intein solubilization partner that is attached to a solid support (Surface). A second fusion protein comprising a C-intein that is complementary to the N-intein in the affinity chromatography matrix is fused to the target protein to be purified (protein of interest) and any other elements required for expression, such as secretion signals.

A description of example embodiments of the invention follows.

I. Definitions

In order that the present disclosure may be more readily understood, certain terms are first defined. Additional definitions are set forth throughout the detailed description. Unless defined otherwise, all technical and scientific terms used herein have the same meaning as commonly understood by one of ordinary skill in the art to which this invention pertains.

The terms "biomolecule of interest" and "target molecule" are used interchangeably herein to refer to a biological molecule (e.g., protein), material or macromolecular assembly, which is to be, e.g., purified or removed from a mixture (e.g., a crude protein mixture). Exemplary biomolecules of interest include, for example, recombinant peptides and proteins, including antibodies (e.g., monoclonal antibodies), vaccines, viruses, and other macromolecular assemblies, such as virus-like particles and nanoparticles that may incorporate both biomolecular and synthetic components. By way of example, biomolecules of interest can include proteins and biomolecular assemblies (e.g., produced by recombinant DNA technology), such as, e.g., hormones (e.g. insulin, human growth hormone, erythropoietin, interferons, granulocyte colony stimulating factor, tissue plasminogen activator), monoclonal antibodies (mAbs) and mAb-derivatives (e.g., bi-specific mAbs, Fabs, scFvs, shark and camelid antibodies), scaffold-derived therapeutics (e.g., DARPins, Affibodies, anticalins), therapeutic enzymes (e.g., alpha galactosidase A, alpha-L-iduronidase, N-acetylgalactosamine-4-sulfatase, glucocerebrosidase), toxins (e.g. botulinum, CRM 197, ricin), recombinant vaccines (e.g., anthrax, diphtheria, tetanus, pneumonia, hepatitis B virus, human papilloma virus), virus-like particles (e.g., hepatitis B, human papilloma, influenza, parvovirus, Norwalk viruses), as well as industrial enzymes (e.g., papain, bromelain, trypsin, proteinase K, BENZONASE™ enzyme, DENERASE™ enzyme, urease, pepsin, etc.) and diagnostic reagents (e.g., glucose and lactate dehydrogenase, DNA polymerases, alkaline phosphatase, horseradish peroxidase, restriction enzymes, hybridoma-derived antibodies, etc.). In a particular embodiment, the target molecule is an antibody (e.g., a monoclonal antibody) to a therapeutic target.

The term "fusion protein" refers to a naturally occurring, synthetic, semi-synthetic or recombinant single protein molecule that comprises all or a portion of two or more heterologous polypeptides joined by peptide bonds.

The term "peptidic", as used herein, refers to peptides and proteins longer than two amino acids in length that may also incorporate non-amino acid molecules (e.g. chromaphores, drugs, toxins, imaging contrast agents, etc.)

The term "polypeptide" refers to a polymer of amino acids, and not to a specific length; thus, peptides, oligopeptides and proteins are included within the definition of a polypeptide.

The term "split intein", as used herein, refers to a protein, either isolated from nature or created through recombinant DNA technology, that has the following properties: (1) the protein occurs in two halves that interact with high affinity and selectivity; (2) the two halves must contain all intein sequences required for catalytic activity and may also contain appended non-intein peptidic sequences; (3) the protein has enzymatic activity only when the two halves are tightly associated; and (4) the enzymatic activity is site selective peptidic cleavage or ligation that serves to separate intein sequences from non-intein peptidic sequences or ligate the non-intein peptidic sequences into contiguous linear or circular proteins.

The term "complementary inteins" is used herein to refer to the N-intien and C-intein poritons of a split intein pair.

The term "N-intein", as used herein, refers to an intein polypeptide having homology to the N-terminal portion of a single intein poylpeptide, and which associates with a complementary C-intein to form an active intein enzyme.

The term "C-intein", as used herein, refers to an intein polypeptide having homology to the C-terminal portion of a single intein polypetide, and which associates with a complementary N-intein to form an active intein enzyme.

The term "extein", as used herein, refers to N- and C-terminal peptidic sequences that are fused to N- and C-inteins in nature and are manipulated (e.g., cleaved or ligated) through the enzymatic action of the split intein.

The term "ligand", as used herein, refers to a molecule that is capable of strong and selective interaction with another, especially when attached to a surface, such as a chromatography resin. In some embodiments of this invention, the ligand may be an N-intein fusion protein described herein.

The term "solubilization partner", as used herein, refers to a protein that, when fused to an N-intein, enhances (e.g., increases, promotes or maintains) the amount of soluble N-intein expressed in *E. Coli* relative to the amount of soluble N-intein expressed in the absence of the solubilization partner. For example, in various embodiments, expressing the N-intein as a fusion protein with a solubilization partner can increase the solubility of the N-intein by at least about 10% (e.g., about 20%, about 30%, about 40%, about 50%, about 60%, about 70%, about 80%, about 90%, or more) relative to solubility of the intein when expressed without the solubilization partner.

In one embodiment, solubilization partner E (SEQ ID NO:25) is fused to an N-intein and the solubility of the resultant fusion protein is used to provide an experimental baseline. This is particularly useful when the N-intein alone is not soluble or stable.

The term "parental molecule" or "wild-type (wt) counterpart" or "wt protein" or "wt domain," as used herein, is intended to refer to a corresponding protein (e.g., N-intein, N-intein solubilization partner), or a domain of a protein, in its substantially native form, which is generally used as a control herein.

The term "sequence identity" means that two nucleotide or amino acid sequences, when optimally aligned, such as by the programs GAP or BESTFIT using default gap weights, share at least 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

The term "chromatography," as used herein, refers to a dynamic separation technique which separates a target molecule of interest from other molecules in the mixture and allows it to be isolated. Typically, in a chromatography method, a mobile phase (liquid or gas) transports a sample containing the target molecule of interest across or through a stationary phase (normally solid) medium. Differences in partition or affinity to the stationary phase separate the different molecules while mobile phase carries the different molecules out at different time.

The term "affinity chromatography," as used herein, refers to a mode of chromatography where a target molecule to be separated is isolated by its interaction with a molecule (e.g., an affinity chromatography ligand according to this invention comprising an N-intein and N-intein solubilization factor) which specifically interacts with the target molecule. In one embodiment, affinity chromatography involves the addition of a sample containing a target molecule (e.g., an immunoglobulin or an Fc-containing protein) to a solid support which carries on it an N-intein-based ligand, as described herein.

The term "affinity matrix" or "affinity chromatography matrix," as used interchangeably herein, refers to a chromatographic support onto which an affinity chromatography ligand (e.g., N-intein fusion protein or a domain thereof) is attached. The ligand is capable of binding to a molecule of interest through affinity interaction (e.g., a complementary C-intein fusion protein) which is to be purified or removed from a mixture.

The term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by .beta.-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

"Antibodies" or "immunoglobulins" may be monoclonal or polyclonal and may exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fc and/or Fv fragments.

The terms "polynucleotide" and "nucleic acid molecule," used interchangeably herein, refer to polymeric forms of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically or biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T, C and G, but also includes any of their analogs or modified forms of these bases, such as methylated nucleotides, internucleotide modifications such as uncharged linkages and thioates, use of sugar analogs, and modified and/or alternative backbone structures, such as polyamides. In a particular embodiment, a nucleic acid molecule comprises a nucleotide sequence encoding an N-intein fusion protein or a variant thereof, as described herein.

II. Intein-Based Fusion Proteins

Inteins are a class of autocatalytic enzymes discovered in 1990 that contain both protease and ligase activities that function in the natural life cycle of these molecules. It has been demonstrated that intein reagents have utility for the cleavage, ligation, and circularization of peptidic substrates. In 1998, a new class of inteins termed "split inteins" was discovered where the enzyme occurs naturally in two parts, termed the N-intein and C-intein (complementary half inteins). While split inteins have been found in a broad variety of lower prokaryotes (Zettler J., et al., *FEBS Letters*, 553:909-914 (2009); Dassa. B., et al., *Biochemistry*, 46:322-330 (2007); Choi J., et al., *J Mol Biol.* 556: 1093-1106 (2006); Caspi, et al., *Mol Microbiol*, 50: 1569-1577 (2003); Liu X. and Yang J., *J Biol Chem.*, 275:26315-26318 (2003); Wu H., et al., *Proc Natl Acad Sci USA*. 5:9226-9231 (1998)), no split inteins have been identified in eukaryotes (see the intein database maintained by New England Biolabs (www.inteins.com)). Two split inteins have recently been characterized that are both extremely fast and fairly promiscuous with respect to adjoining extein sequences. One class is the Npu DnaE intein (Iwai I., et al., *FEBS Letters* 550: 1853-1858 (2006); Zettler J., et al., *FEBS Letters*, 553:909-914 (2009)) and the other, the GP41 split inteins identified from metagenomic data (Carvajal-Vallejos P., et al., *J. Biol. Chem.* 287: 28686-28696 (2012); International PCI Publication No. WO2013045632).

The N- and C-inteins, with attached exteins (the two half proteins that will be joined by intein activity), associate extremely specifically and tightly through multiple inter-domain interactions to form the active intein enzyme (Shah N. H., et al., *J. Amer. Chem. Soc.* 135: 18673-18681; Dassa B., et al., *Nucl. Acids Res.*, 37:2560-2573 (2009)). In addition to the ligase and protease activities present in the first class of inteins, the split inteins have utility in affinity separations due to the tight and selective interaction of the N- and C-intein domains.

The present invention is based, in part, on the discovery that expressing intein polypeptides as fusion proteins with certain heterologous proteins, referred to herein as solubilization partners, increases the solubility of the intein, thereby rendering the intein suitable as a reagent for affinity chromatography and other protein purification and modification applications that can be practiced on a small or large scale. More specifically, the invention provides highly soluble fusion proteins comprising an N-intein polypeptide and an N-intein solubilization partner capable of forming an active intein complex by associating with a complementary C-intein polypeptide. The invention also provides fusion proteins comprising a C-intein polypeptide and a target molecule, wherein the fusion protein is capable of associating with another fusion protein comprising a complementary N-intein polypeptide and an N-intein solubilization partner.

Accordingly, in one embodiment, the present invention relates to a fusion protein comprising all, or a portion of, an N-intein polypeptide and an N-intein solubilization partner. A variety of N-intein polypeptides are known in the art. Exemplary N-inteins include the N-inteins shown in Table 1 and others described elsewhere herein. The N-inteins disclosed herein, and other N-inteins known in the art, as well as variants of such N-inteins having at least about 75% sequence identity (e.g., at least about 80%, at least about 90%, at least about 95%, at least about 96%, at least about 97%, at least about 98%, at least about 99% sequence identity) to a wild type N-intein, can be included in the fusion proteins described herein.

The first amino acid in an intein N-terminal domain is typically highly conserved and can be important for the protein splicing reaction. However, in some embodiments, the first amino acid in an intein N-terminal domain (e.g., a cysteine, a serine) can be substituted with an amino acid (e.g., an amino acid other than cysteine or serine) that prevents or decreases cleavage between the intein and a heterologous polypeptide. In a particular embodiment, the first amino acid in an intein N-terminal domain is substituted with an alanine.

In a particular embodiment, the N-intein fusion proteins described herein comprise the wild type GP41-1 N-intein (SEQ ID NO:1 or SEQ ID NO: 29) or a variant thereof. Suitable variant GP41-1 N-inteins can have at least about 75% sequence identity (e.g., at least about 80%, at least about 90%, at least about 95%, at least about 96%, at least about 97%, at least about 98%, at least about 99% sequence identity) to the wild type GP41-1 N-intein (SEQ ID NO:1). Particular examples of variant GP41-1 N-inteins for inclusion in the fusion proteins of the invention include the GP41-1 variants assigned SEQ ID NOs:2-8 herein. In certain embodiments, the GP41-1 N-intein variant lacks cysteine residues. In a particular embodiment, one or more cysteine residues that occur naturally in the GP41-1 N-intein are deleted. In another embodiment, one or more cysteine residues that occur naturally in the GP41-1 N-intein (positions 7, 65 and 89 of SEQ ID NO:1) are substituted with another amino acid residue (e.g., threonine, lysine, or asparagine). In a one embodiment, the cysteine residue that occurs naturally in the GP41-1 N-intein at position 65 of SEQ ID NO:1 is substituted with another amino acid residue (e.g., serine, threonine). In a particular embodiment, the cysteine residue at position 65 of SEQ ID NO:1 is substituted with threonine. In yet another embodiment, the cysteine residue that occurs naturally in the GP41-1 N-intein at position 89 of SEQ ID NO:1 is substituted with another amino acid residue (e.g., methionine, tyrosine). In a particular embodiment, the cysteine residue at position 89 of SEQ ID NO:1 is substituted with methionine. In some embodiments, the GP41-1 variant is the GP41-1 NINTΔA_TM N-intein variant (SEQ ID NO: 6) or the GP41-1 NINTΔA_TK N-intein variant (SEQ ID NO:8).

In some embodiments, the GP41-1 N-intein variant lacking some or all cysteine residues are at least 2 fold, at least 3 fold, at least 4 fold, at least 5 fold, at least 6 fold, at least 7 fold, at least 8 fold, at least 9 fold, or at least 10 fold more active than the natural GP41-1 N-intein in ligation or cleavage reactions. Intein activity, either cleavage or ligation, can generally be analyzed using SDS gel electrophoresis under reducing conditions (e.g. Zettler J., Schatz V., Mootz H. D., FEBS Letters 583: 909-914, 2009; Aranko A. S., Züger S, Buchinger E, Iwai H, PLoS ONE 4: e5185, 2009). Briefly, intein reactions, generally a time course, are stopped by the addition of SDS gel loading buffer containing a reducing agent (e.g., dithiothreitol or β-mercaptoethanol), the samples are boiled to fully denature them, and then are loaded onto a polyacrylamide gel containing SDS along with appropriate protein size markers. After electrophoresis is completed, proteins in the reaction have been separated according to their molecular weights, and may be visualized by staining with traditional or fluorescent dyes. The amounts of the various intermediates and products as a function of time can be quantitated by densitometry and intensities as a function of time converted into enzymatic rates (kobs) through application of a curve fitting program.

TABLE 1

Exemplary GP41-1 Split Inteins and Variants Thereof

| SEQ ID NO: | name | sequence |
|---|---|---|
| 1 | GP41-1 N-intein | mtrsgyCLDLKTQVQTPQGMKEISNIQVGDLVLS NTGYNEVLNVFPKSKKKSYKITLEDGKEIICSEE HLFPTQTGEMNISGGLKEGMCLYVKEgg |
| 2 | GP41-1 NINTΔA_CC N-intein vanant | mtrsgyALDLKTQVQTPQGMKEISNIQVGDLVLS NTGYNEVLNVFPKSKKKSYKITLEDGKEIICSEE HLFPTQTGEMNISGGLKEGMCLYVKEgg |
| 3 | GP41-1 NINTΔA_AC N-intein variant | mtrsgyALDLKTQVQTPQGMKEISNIQVGDLVLS NTGYNEVLNVFPKSKKKSYKITLEDGKEIIASE EHLFPTQTGEMNISGGLKEGMCLYVKEgg |
| 4 | GP41-1 NINTΔA_CK N-intein variant | mtrsgyALDLKTQVQTPQGMKEISNIQVGDLVLS NTGYNEVLNVFPKSKKKSYKITLEDGKEIICSEE HLFPTQTGEMNISGGLKEGMKLYVKEgg |
| 5 | GP41-1 NINTΔA_AM N-intein variant | mtrsgyALDLKTQVQTPQGMKEISNIQVGDLVLS NTGYNEVLNVFPKSKKKSYKITLEDGKEIIASE EHLFPTQTGEMNISGGLKEGMMLYVKEgg |

TABLE 1-continued

Exemplary GP41-1 Split Inteins and Variants Thereof

| SEQ ID NO: | name | sequence |
|---|---|---|
| 6 | GP41-1 NINTΔA_TM N-intein variant | mtrsgyALDLKTQVQTPQGMKEISNIQVGDLVLS NTGYNEVLNVFPKSKKKSYKITLEDGKEIITSEE HLFPTQTGEMNISGGLKEGMMLYVKEgg |
| 7 | GP41-1 NINTΔA_AK N-intein variant | mtrsgyALDLKTQVQTPQGMKEISNIQVGDLVLS NTGYNEVLNVFPKSKKKSYKITLEDGKEIIASE EHLFPTQTGEMNISGGLKEGMKLYVKEgg |
| 8 | GP41-1 NINTΔA_TK N-intein variant | mtrsgyALDLKTQVQTPQGMKEISNIQVGDLVLS NTGYNEVLNVFPKSKKKSYKITLEDGKEIITSEE HLFPTQTGEMNISGGLKEGMKLYVKEgg |
| 9 | GP41-1 C-intein (CINT) | MGKNSMMLKKILKIEELDERELIDIEVSGNHLF YANDILTHN |
| 10 | GP41-1 C-intein-thioredoxin fusion protein (CINT_TRX) (thioredoxin portion is underlined) | MGKNSMMLKKILKIEELDERELIDIEVSGNHLF YANDILTHNMSDKIIHLTDDSFDTDVLKADGAI LVDFWAEWCGPCKMIAPILDEIADEYQGKLTV AKLNIDQNPGTAPKYGIRGIPTLLLFKNGEVAA TKVGALSKGQLKEFLDANLAHHHHHH |

For SEQ ID Nos: 1-8, non-intein sequences are indicated using lower case text and intein sequences are indicated by upper case text for SEQ ID NO: 1-8.

Typically, N-intein polypeptides have poor solubility when expressed in common expression systems, such as *E. Coli*. The present invention circumvents this problem by, for example, expressing the N-intein as a fusion protein with an N-intein solubilization partner, which increases the solubility of the N-intein (e.g., when expressed in *E. Coli*). Preferably, the N-intein solubilization partner increases the solubility of the N-intein polypeptide such that less than about 25% by mass of the resultant fusion protein is present in inclusion bodies following production in the expression system (e.g., *E. Coli*). The percentage by mass of an expressed protein that is present in inclusion bodies following production in an expression system can be readily determined by a person of ordinary skill in the art using standard techniques and reagents.

A person of ordinary skill in the art can readily select potential solubilization partners that may increase the solubility of a given N-intein using techniques known in the art and described herein. For example, the probability of generating a soluble product upon overexpression in an expression system (e.g., *E. Coli*) can be calculated using the algorithm of Wilkinson and Harrison (Wilkinson D L and Harrison R G, Bio/Technology, 9: 443, 1991). The prediction of whether the protein contains a functional secretion signal can be performed using the SignalP 4.1 algorithm available from the Center for Biological Sequence Analysis at the Technical University of Denmark (genome.cbs.dtu.dk/services/SignalP/). Also see methods described in Examples 1-3 disclosed herein. Ultimately, solubilization partners that provide both optimal enhancement of solubility while allowing maximal intein catalytic activity must be selected from the candidate solubilization partners through experimental screening.

N-intein solubilization partners having certain physical properties are particularly suitable for inclusion in the fusion proteins of the invention. Such physical properties include, but are not limited to, a molecular weight of less than about 15 kDa, an Aliphatic Index (AI) value less than about 60, and a GRAVY value that is less than −1. Each of these properties can be determined for a given solubilization partner by one of ordinary skill in this art using standard assays and techniques, for example, using the online ProtParam tool (web.expasy.org/tools/protparam/) that is part of the SwissProt ExPASy suite of bio informatics tools.

The Grand average of hydropathicity (GRAVY) (Kyte J and Doolittle R F., *J. Mol. Biol.* 157:105, 1982) of a linear polypeptide sequence is calculated as the sum of hydropathy values of all amino acids, divided by the number of residues in the sequence. Increasing positive score indicates greater hydrophobicity. The calculation is based on the Kyte-Doolittle scale. GRAVY is a simple method for displaying the hydropathic character of a protein.

| | |
|---|---|
| Alanine | 1.8 |
| Arginine | −4.5 |
| Asparagine | −3.5 |
| Aspartic acid | −3.5 |
| Cysteine | 2.5 |
| Glutamine | −3.5 |
| Glutamic acid | −3.5 |
| Glycine | −0.4 |
| Histidine | −3.2 |
| Isoleucine | 4.5 |
| Leucine | 3.8 |
| Lysine | −3.9 |
| Methionine | 1.9 |
| Phenylalanine | 2.8 |
| Proline | −1.6 |
| Serine | −0.8 |
| Threonine | −0.7 |
| Tryptophan | −0.9 |
| Tyrosine | −1.3 |
| Valine | 4.2 |

In various embodiments, the N-intein fusion proteins described herein have a GRAVY value that is less than −1.

The Aliphatic Index (Ikai, A J., *J. Biochem.* 88:1895, 1980) of a protein is defined as the relative volume occupied by aliphatic side chains (alanine, valine, isoleucine, and leucine). It may be regarded as a positive factor for the increase of thermostability of globular proteins. The aliphatic index of a protein is calculated according to the following formula: Aliphatic index=X(Ala)+a*X(Val)+b*

(X(Ile)+X(Leu)). *The coefficients a and b are the relative volume of valine side chain (a=2.9) and of Leu/Ile side chains (b=3.9) to the side chain of alanine. The probability of generating a soluble product upon overexpression in *E. Coli* can also be calculated using the algorithm of Wilkinson and Harrison (Wilkinson D L and Harrison R G., *Bio/Technology*, 9: 443, 1991). Other available algorithms do not necessarily give similar results. In various embodiments, the N-intein fusion proteins described herein have an Aliphatic Index (AI) value less than about 60, and a GRAVY value that is less than −1.

Preferably, the N-intein solubilization partner has a molecular weight of less than about 15 kDa, an Aliphatic Index value less than about 60.

Examples of particular N-intein solubilization partners are disclosed in Table 2.

TABLE 2

Exemplary N-intein Solubilization Partners

| SEQ ID NO: | Name | GID | Sequence |
|---|---|---|---|
| 11 | Solubilization partner 46: Qin prophage; cold shock-induced protein | 170081219 | MREYPNGEKTHLTVMAAGFPSL TGDHKVIYVAADRHVTSEEILE AAIRLLS |
| 12 | Solubilization partner 206: hypothetical protein ECDH10B_1576 [*Escherichia coli* str. K-12 sub str. DH10B] | 170081120 | MSHLDEVIARVDAAIEESVIAH MNELLIALSDDAELSREDRYTQ QQRLRTAIAHHGRKHKEDMEA RHEQLTKGGTIL |
| 13 | Solubilization partner 246: hypothetical protein ECDH10B_1388 [*Escherichia coli* str. K-12 sub str. DH10B] | 170080950 | MNKETQPIDRETLLKEANKIIRE HEDTLAGIEATGVTQRNGVLVF TGDYFLDEQGLPTAKSTAVFNM FKHLAHVLSEKYHLVD |
| 14 | Solubilization partner 51: hypothetical protein ECDH10B_0422 [*Escherichia coli* str. K-12 sub str. DH10B] | 170080051 | MSLENAPDDVKLAVDLIVLLEE NQIPASTVLRALDIVKRDYEKKL TRDDEAEK |
| 15 | Solubilization partner 138: putative stress-response protein [*Escherichia coli* str. K-12 substr. DH10B] | 170083502 | MNKDEAGGNWKQFKGKVKEQ WGKLTDDDMTIIEGKRDQLVG KIQERYGYQKDQAEKEVVDWE TRNEYRW |
| 16 | Solubilization partner 138 GKL22GCKL: putative stress-response protein [*Escherichia coli* str. K-12 sub str. DH10B] | NA | MNKDEAGGNWKQFKGKVKEQ WG<u>C</u>KLTDDDMTIIEGKRDQLV GKIQERYGYQKDQAEKEVVDW ETRNEYRW |
| 17 | Solubilization partner 138 GYQ48GCYQ: putative stress-response protein [*Escherichia coli* str. K-12 sub str. DH10B] | NA | MNKDEAGGNWKQFKGKVKEQ WGKLTDDDMTIIEGKRDQLVG KIQERYG<u>C</u>YQKDQAEKEVVDW ETRNEYRW |
| 18 | Solubilization partner 138 GYQ48GCGY: putative stress-response protein [*Escherichia coli* str. K-12 sub str. DH10B] | NA | MNKDEAGGNWKQFKGKVKEQ WGKLTDDDMTIIEGKRDQLVG KIQERYG<u>CG</u>YQKDQAEKEVVD WETRNEYRW |
| 19 | Solubilization partner 342: hypothetical protein ECDH10B_2487 [*Escherichia coli* str. K-12 sub str. DH10B] | 170081941 | MIAEFESRILALIDGMVDHASDD ELFASGYLRGHLTLAIAELESGD DHSAQAVHTTVSQSLEKAIGAG ELSPRDQALVTDMWENLFQQA SQQ |
| 20 | Solubilization partner 368: putative sigma(54) modulation protein [*Escherichia coli* str. K-12 sub str. DH10B] | 170082737 | MQLNITGNNVEITEALREFVTA KFAKLEQYFDRINQVYVVLKVE KVTHTSDATLHVNGGEIHASAE GQDMYAAIDGLIDKLARQLTKH KDKLKQH |

TABLE 2-continued

Exemplary N-intein Solubilization Partners

| SEQ ID NO: | Name | GID | Sequence |
|---|---|---|---|
| 21 | Solubilization partner A: EspA component of the type 3 secretion system | 9626250 | MDTSNATSVVNVSASSSTSTIYD LGNMSKDEVVKLFEELGVFQA AILMFSYMYQAQSNLSIAKFAD MNEASKASTTAQKMANLVDAK IADVQSSTDKNAKAKLPQDVID YINDPRNDISVTGISDLSGDLSA GDLQTVKAAISAKANNLTTVVN NSQLEIQQMSNTLNLLTSARSD VQSLQYRTISAISLGK |
| 22 | Solubilization partner B: fh8 protease from Fasciola hepatica (HiTag) | 147611 | MPSVEVEKLLHVLDRNGDGKV SAEELKAFADDSKYPLDSNKIK AFIKEHDKNKDGKLDLKELVSIL SS |
| 23 | Solubilization partner C: fh8 protease from Fasciola hepatica (HiTag) | 387618410 | MPSVEVEKLLH |
| 24 | Solubilization partner D: glutathione S-transferase | 251787291 | MGQLIDGVWHDTWYDTKSTGG KFQRSASAFRNWLTADGAPGPT GKGGFAAEKDRYHLYVSLACP WAHRTLEVIRKLKGLEPEISVSV VNPLMLENGWTFDDSFPGATG DTLYQHEFLYQLYLHADPHYSG RVTVPVLWDKKNHTIVSNESAE IIRMENTAFDALGAKAGDYYPP ALQPKIDELNGWIYDTVNNGVY KAGFATSQQAYDEAVAKVFESL ARLEQILGQHRYLTGNQLTEADI RLWTTLVRFDPVYVTHFKCDK HRISDYLNLYGFLRDIYQMPGIA ETVNEDHIRNHYERSHKTINPTG IISIGPWQDLDEPHGRDVRFG |
| 25 | Solubilization partner E: head-DNA stabilization protein [Enterobacteria phage lambda] | 410480759 | MASWSHPQFEKASKETFTHYQP QGNSDPAHTATAPGGLSAKAPA MTPLMLDTSSRKLVAWDGTTD GAAVGILAVAADQTSTTLTFYK SGTFRYEDVLWPEAASDETKKR TAFAGTAISIV |
| 26 | Solubilization partner F: maltose binding protein | 218465276 | MKIKTGARILALSALTTMMESA SALAKIEEGKLVIWINGDKGYN GLAEVGKKFEKDTGIKVTVEHP DKLEEKFPQVAATGDGPDIIFW AHDRFGGYAQSGLLAEITPDKA FQDKLYPFTWDAVRYNGKLIAY PIAVEALSLIYNKDLLPNPPKTW EEIPALDKELKAKGKSALMFNL QEPYFTWPLIAADGGYAFKYEN GKYDIKDVGVDNAGAKAGLTF LVDLIKNKHMNADTDYSIAEAA FNKGETAMTINGPWAWSNIDTS KVNYGVTVLPTFKGQPSKPFVG VLSAGINAASPNKELAKEFLEN YLLTDEGLEAVNKDKPLGAVAL KSYEEELAKDPRIAATMENAQK GEIMPNIPQMSAFWYAVRTAVI NAASGRQTVDEALKDAQTRITK |
| 27 | Solubilization partner G: thioredoxin | 218465276 | MSDKIIHLTDDSFDTDVLKADG AILVDFWAEWCGPCKMIAPILD EIADEYQGKLTVAKLNIDQNPG TAPKYGIRGIPTLLLFKNGEVAA TKVGALSKGQLKEFLDANLA |

TABLE 2-continued

Exemplary N-intein Solubilization Partners

| SEQ ID NO: | Name | GID | Sequence |
|---|---|---|---|
| 28 | Solubilization partner H: transcription termination factor NusA | 387509083 | MNKEILAVVEAVSNEKALPREK IFEALESALATATKKKYEQEIDV RVQIDRKSGDFDTFRRWLVVDE VTQPTKEITLEAARYEDESLNLG DYVEDQIESVTFDRITTQTAKQV IVQKVREAERAMVVDQFREHE GEIITGVVKKVNRDNISLDLGNN AEAVILREDMLPRENFRPGDRV RGVLYSVRPEARGAQLFVTRSK PEMLIELFRIEVPEIGEEVIEIKAA ARDPGSRAKIAVKTNDKRIDPV GACVGMRGARVQAVSTELGGE RIDIVLWDDNPAQFVINAMAPA DVASIVVDEDKHTMDIAVEAGN LAQAIGRNGQNVRLASQLSGWE LNVMTVDDLQAKHQAEAHAAI DTFTKYLDIDEDFATVLVEEGFS TLEELAYVPMKELLEIEGLDEPT VEALRERAKNALATIAQAQEES LGDNKPADDLLNLEGVDRDLAF KLAARGVCTLEDLAEQGIDDLA DIEGLTDEKAGALIMAARNICW FGDEA |

"GID" refers to the GenBank ID (www.ncbi.nlm.nih.gov/genbank). Solubilization partners A-H are known solubilization partners, many of which have been incorporated into commercially available fusion systems to increase the yield and solubility of recombinant proteins produced in *E. coli*. Amino acids that have been artificially substituted or inserted into the parent sequence are highlighted in bold and underlined.

In a particular embodiment, the N-intein solubilization partner is, or comprises, all or a portion of solubilization partner 138 (SEQ ID NO:15), or a variant thereof (e.g., solubilization partner 138 GKL22GCKL (SEQ ID NO:16); solubilization partner 138 GYQ48GCYQ (SEQ ID NO:17); solubilization partner 138 GYQ48GCGY (SEQ ID NO:18)).

Methods of preparing fusion, or chimeric, proteins are well known in the art including, but not limited to, standard recombinant DNA techniques. For example, DNA fragments coding for different protein sequences (e.g., an N-intein and an N-intein solubilization partner; a C-intein and a target molecule) are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., *Current Protocols in Molecular Biology*, 1992). Moreover, many expression vectors are commercially available that already encode a fusion moiety (e.g., a GST moiety, an Fc moiety).

Preferably, the fusion protein is expressed from an encoding nucleic acid in transiently or stably transfected or transformed prokaryotic or eukaryotic host cells or organisms. Common host cells or organisms for expression of recombinant proteins include, for example, *Escherichia Coli*, *Corynebacterium glutamicum*, *Pseudomonas fluorescens*, *Lactococcus lactis*, *Pichia pastoris*, *Saccharomyces cerevisiae*, *Zea maize*, *Nicotinia tabacum*, *Daucus carota*, SF9 cells, CHO cells (e.g., CHO DG44 cells, CHO DXB11 cells), NS0 cells, HEK 293 cells, and whole animals such as cows and goats. In an embodiment, the N-intein fusion protein is expressed in *E. Coli*. The expressed N-intein fusion protein can then be purified away from contaminating cellular proteins using conventional separation and chromatographic methods, such as clarification by depth filtration, purification by anion and cation exchange chromatography, and concentration by ultrafiltration.

The heterologous protein (e.g., N-intein solubilization partner, target molecule) can be fused to either end of the intein polypeptide. In one embodiment, an N-intein solubilization partner is joined to the N-terminal end of an N-intein polypeptide. In another embodiment, an N-intein solubilization partner is joined to the C-terminal end of an N-intein polypeptide.

In some embodiments, the intein polypeptide (e.g., N-intein, C-intein) and heterologous protein (e.g., N-intein solubilization partner, target molecule) are linked directly via a peptide bond. In other embodiments, the fusion protein includes a spacer, or linker, molecule between the intein polypeptide (e.g., N-intein, C-intein) and heterologous protein (e.g., N-intein solubilization partner, target molecule). Suitable spacer/linker molecules are known in the art.

In the fusion proteins described herein, the intein N-terminal domain can be fused either directly (e.g., via a peptide bond) or indirectly (e.g., via a linker amino acid sequence) to a heterologous polypeptide. Thus, in some embodiments, a heterologous polypeptide is fused either directly or indirectly to the N-terminus of an intein N-terminal domain. In certain embodiments, the first amino acid of the heterologous polypeptide is selected from the group consisting of Met, Cys, Thr, Arg, Lys, Ser, Gln, His, Ala, Tyr, Phe, Asn, Trp, Val, Leu, Asp, He, Gly, Glu and Pro.

In some embodiments, the fusion protein comprises a linker between the heterologous polypeptide and the intein sequence. For example, the fusion protein can comprise a linker between the C-terminus of the heterologous protein and the N-terminus of the N-terminal domain of the intein. The linker can be, for example, from about 1 to about 10 amino acids in length. In some embodiments, the linker can be about 1 to about 5 amino acids in length. For example, the linker can contain 1, 2, 3, 4, or 5 amino acids. In some embodiments, the last amino acid of the linker contacting the heterologous polypeptide and the N-terminus of the N-terminal domain of an intein is selected from the group consisting of Met, Cys, Thr, Arg, Lys, Ser, Gln, His, Ala, Tyr, Phe, Asn, Trp, Val, Leu, Asp, Ile, Gly, Glu and Pro.

In some embodiments, the linker can comprise an extein sequence. In some embodiments, the linker can comprise a native extein sequence. In some embodiments, the extein comprises a sequence selected from the group consisting of SEQ ID NOs: 4, 8, 13, 17, 21, 25, 35, and 39 from WO201345632. In some embodiments, a linker comprising amino acids of an extein comprises, for example, the first (i.e., N-terminal) about 1 to about 5 amino acids of a sequence selected from the group consisting of SEQ ID NOs: 4, 8, 13, 17, 21, 25, 35, and 39. In some embodiments, the linker comprises about 1, 2, 3, 4, or 5 amino acids of a sequence selected from the group consisting of SEQ ID NOs: 4, 8, 13, 17, 21, 25, 35, and 39. In some embodiments, a fusion protein comprises an intein domain and an extein domain that are found together in nature (e.g., a GP41-1 N-intein and GP41-1 C-intein). In other embodiments, a fusion protein comprises an intein domain and an extein domain that is not found together with that particular intein domain in nature, also referred to herein as a "heterologous extein domain." By way of example, a fusion protein can comprise a GP41-1 intein domain and an IMPDH extein domain.

The fusion proteins of the invention can optionally further include one or more detectable labels. Labels suitable for use according to the present invention are known in the art and generally include any molecule that, by its chemical nature, and whether by direct or indirect means, provides an identifiable signal allowing detection of a protein. Thus, for example, fusion proteins may be labeled in a conventional manner, such as with specific reporter molecules, fluorophores, radioactive materials, or enzymes (e.g., peroxidases, phosphatases). In a particular embodiment, the fusion proteins include one or more fluorescent dyes as detectable labels. Standard methods for modifying a protein to include a detectable label are known in the art.

In various embodiments, the invention further relates to an isolated nucleic acid which comprises a nucleotide sequence encoding a fusion protein of the invention, an expression vector comprising such nucleic acids and a host cell carrying such expression vectors.

III. Affinity Chromatography Matrices Comprising N-Intein Fusion Proteins

The fusion proteins described herein containing N-intein polypeptides and N-intein solubilization partners have utility as, inter alia, ligands for affinity chromatography applications. Accordingly, the present invention, in certain embodiments, provides affinity chromatography matrices comprising a fusion protein comprising an N-intein polypeptide and an N-intein solubilization partner attached to a solid support.

In a particular embodiment, the solid support is a chromatography resin. In a certain embodiment, the chromatography resin includes a hydrophilic polyvinyl ether base. Suitable chromatography resins having a hydrophilic polyvinyl ether base include, but are not limited to, ESHMUNO® resins (EMD Millipore Corporation).

In another embodiment, the chromatography resin is a synthetic methacrylate-based polymeric medium (e.g., beads with a particle size in the range of about 20-40 μm or about 40-90 μmm). In some embodiments, the chromatography resin has carboxylic acid functionality. Suitable chromatography resins having carboxylic acid functionality include, but are not limited to, FRACTOGEL® COO resins (EMD Millipore Corporation).

Other suitable solid supports for affinity chromatography matrices of the invention can include, for example, controlled pore glass, silica, zirconium oxide, titanium oxide, agarose, polymethacrylate, polyacrylate, polyacrylamide, polyvinyl alcohol and polystyrene, as well as derivatives thereof (e.g., alloys thereof).

A porous material used as a solid support may be comprised of a hydrophilic compound, a hydrophobic compound, an oleophobic compound, an oleophilic compound or any combination thereof. The porous material may be comprised of a polymer or a copolymer. Examples of suitable porous materials, include, but are not limited to polyether sulfone, polyamide, e.g., nylon, polysaccharides such as, for example, agarose and cellulose, polyacrylate, polymethacrylate, polyacrylamide, polymethacrylamide, polytetrafluoroethylene, polysulfone, polyester, polyvinylidene fluoride, polypropylene, polyethylene, polyvinyl alcohol, polycarbonate, polymer of a fluorocarbon, e.g., poly (tetrafluoroethylene-co-perfluoro(alkyl vinyl ether)), glass, silica, zirconia, titania, ceramic, metal and alloys thereof.

The porous material may be comprised of an organic or inorganic molecule or a combination of organic and inorganic molecules and may be comprised of one or more functional groups, e.g., a hydroxyl group, a thiol group, an amino group, a carbonyl group, or a carboxylic acid group, suitable for reacting, e.g., forming covalent bonds for further chemical modification, in order to covalently bind to a protein. In another embodiment, the porous material may not possess a functional group but can be coated with a layer of material that bears functional groups such as, a hydroxyl group, a thiol group, an amino acid group, a carbonyl group, or a carboxylic acid group.

In some embodiments, a conventional affinity separation matrix is used, e.g., of organic nature and based on polymers that expose a hydrophilic surface to the aqueous media used, e.g., expose hydroxy (—OH), carboxy (—COOH), carbonyl (—CHO, or RCO—R'), carboxamido (—CONH$_2$, possibly in N-substituted forms), amino (—NH$_2$, possibly in substituted form), oligo- or polyethylenoxy groups on their external and, if present, also on internal surfaces. In one embodiment, the polymers may, for instance, be based on polysaccharides, such as dextran, starch, cellulose, pullulan, agarose etc, which advantageously have been cross-linked, for instance with bisepoxides, epihalohydrins, allyl bromide, allyglycidyl ether, 1,2,3-trihalo substituted lower hydrocarbons, to provide a suitable porosity and rigidity. In another embodiment, the solid support comprises porous agarose beads. The various supports used in the present invention can be readily prepared according to standard methods known in the art, such as, for example, inverse suspension gelation described, e.g., in Hjerten, *Biochim Biophys Acta* 79(2), 393-398 (1964). Alternatively, the base matrices can be commercially available products, such as SEPHAROSE™ FastFlow media (GE Healthcare, Uppsala, Sweden). In some embodiments, particularly advantageous for large-scale separations, the support is adapted to increase its rigidity, and hence renders the matrix more suitable for high flow rates.

Alternatively, the solid support can be based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilized to expose hydrophilic groups as defined above to a surrounding aqueous liquid. Such polymers can be easily produced according to standard methods, see e.g., Arshady, *Chimica e L'Industria* 70(9), 70-75 (1988). Alternatively, a commercially available product, such as SOURCE™ (GE Healthcare, Uppsala, Sweden) and POROS resin (Applied Biosystems, Foster City, Calif.) may be used.

In yet other embodiments, the solid support comprises a support of inorganic nature, e.g., silica, zirconium oxide, titanium oxide and alloys thereof. The surface of inorganic matrices is often modified to include suitable reactive groups. Examples include CM Zirconia (Ciphergen-BioSepra (Cergypontoise, France)) and CPG® supports (Millipore Corporation).

In some embodiments, the solid support may, for instance, be based on zirconia, titania or silica in the form of controlled pore glass, which may be modified to either contain reactive groups and/or sustain caustic soaking, to be coupled to ligands.

Exemplary solid support formats include, but are not limited to, a bead (spherical or irregular), a hollow fiber, a solid fiber, a pad, a gel, a membrane, a cassette, a column, a chip, a slide, a plate or a monolith.

With respect to the format of a matrix, in one embodiment, it is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batch-wise mode will be used. Also, solid support in forms such as a surface, a chip, a capillary, or a filter may be used.

The matrix could also be in the form of membrane in a cartridge. The membrane could be in flat sheet, spiral, or hollow fiber format.

In certain embodiments, the solid support can be a soluble support, e.g., a soluble polymer or a water soluble polymer. Exemplary soluble supports include, but are not limited to, a bio-polymer such as, e.g., a protein or a nucleic acid. The polymer may also be a synthetic soluble polymer, such as, for example, including but not limited to, a polymer containing negatively charged groups (carboxylic or sulfonic), positively charged groups (quaternary amine, tertiary amine, secondary or primary groups), hydrophobic groups (phenyl or butyl groups), hydrophilic groups (hydroxyl, or amino groups) or a combination of the above. Exemplary synthetic soluble polymers can be found in International PCT Publication No. WO2008091740 and U.S. Publication No. US20080255027, the entire teachings of each of which are incorporated by reference herein.

In some embodiments, the solid support can include an avidin molecule (e.g., streptavidin) and the N-intein fusion protein can comprise a biotin tag (e.g., a biotin molecule covalently attached to the solubilization partner in the fusion protein), such that binding of the fusion protein to the solid support is achieved through interaction of the avidin and biotin molecules.

The N-intein fusion proteins of the invention can be attached to the solid support at only one site in the fusion protein (single point attachment) or at more than one site in the fusion protein (multipoint attachment). Preferably, the N-intein polypeptide in the fusion protein is oriented away from the solid support when the fusion protein is attached to the solid support. For example, unique reactive amino acid groups (e.g., cysteine residues) can be positioned in the solubilization partner at locations that are distal to the active region of the N-intein domain to ensure that the N-intein is directed away from the solid support.

Preferably, the site(s) (e.g., unique reactive amino acid groups) in the fusion protein that are involved in the attachment to the solid support are located exclusively in the N-intein solubilization partner. Accordingly, to achieve this, it may be necessary to modify the N-intein polypeptide to remove the amino acid that provides the unique reactive site (e.g., cysteine), for example, by deletion or substitution of such amino acids wherever they occur in the N-intein. Methods of deleting or substituting amino acids in a protein are well known in the art.

Immobilized N-intein fusion protein may be suitable for column or multi-well chromatographic separations or may be paramagnetic such that it may be captured from solution by application of a magnetic field.

Any suitable technique may be used for attaching a fusion protein described herein to a support, e.g., a solid support including those well-known in the art and described herein. For example, in some embodiments, the fusion protein may be attached to a support via conventional coupling techniques utilizing, e.g., thiol, amino and/or carboxy groups present in the fusion protein. For example, bisepoxides, epichlorohydrin, CNBr, N-hydroxysuccinimide (NHS) etc., are well-known coupling reagents. In some embodiments, a spacer is introduced between the support and the fusion protein, which improves the availability of the fusion protein and facilitates the chemical coupling of the fusion protein to the support.

Attachment of an N-intein fusion protein to a solid support can be achieved via many different ways, most of which are well known in the art, as well as those described herein. See e.g., Hermanson et al., *Immobilized Affinity Ligand Techniques*, Academic Press, pp. 51-136 (1992). For example, protein ligands can be coupled to a solid support via active groups on either the surface of the solid support or the protein ligand, such as, for example, hydroxyl, thiol, epoxide, amino, carbonyl, epoxide, or carboxylic acid group. Attachment can be achieved using known chemistries including, but not limited to, use of cyanogen bromide (CNBr), N-hydroxyl succinimide ester, epoxy (bisoxirane) activation, and reductive amination.

In a particular embodiment, a chromatography resin (e.g., beads) having carboxylic acid (—COOH) or amino (—NH$_2$) groups is used. In a further embodiment, the chromatography resin also has hydroxyl (—OH) groups and/or other functional group that can be converted into —COOH or —NH$_2$ or —OH.

In some embodiments, thiol-directed protein coupling can be used to attached the N-intein fusion protein of the invention to a solid support. Thiol-directed protein coupling has been described in the literature. See, e.g., Ljungquist, et al., *Eur. J. Biochem.* Vol 186, pp. 558-561 (1989). Maleimides are known to react selectively with thiol groups at pH 7.0-7.5. At pH>8, they may also react with amine groups and, in addition, tend to hydrolyze (Greg T. Hermanson, Bioconjugation Techniques, Academic Press, 2008; Ian Johnson, Michelle T. Z. Spence, Molecular Probes Handbook, A Guide to Fluorescent Probes and Labeling Technologies, 2010). Below pH 8, iodoacetamides are also highly selective towards thiol groups (Greg T. Hermanson, Bioconjugation Techniques, Academic Press, 2008; Ian Johnson, Michelle T. Z. Spence, Molecular Probes Handbook, A Guide to Fluorescent Probes and Labeling Technologies, 2010). However, iodoacetamides are intrinsically unstable in light and most commercially available linkers are not water soluble and/or very expensive. Since the selectivity of iodoacetamide towards thiol groups is not superior to maleimide, maleimide is generally the better choice for large scale manufacture.

In some embodiments, the N-intein ligand can be coupled to AMP or iodoacetamide activated FG-COO through a single available sulfhydryl group in the solubilization domain. The ligand density of the derivatised resin can be calculated by measuring depletion of a fusion protein bearing the C-intein from solution. To date, an unoptimized N-intein ligand density of 1 gm/liter of FG-COO has been achieved.

Many proteins have also been successfully coupled to epoxy activated resins, such as FRACTOGEL® Epoxy. The epoxide reacts with primary amino groups, hydroxyl, and sulfhydryl groups and yields very stable affinity matrices (PV Kuznetsov 1993. Pharmaceutical Chemistry Journal 27:439-52).

In some embodiments, the protein ligands can be coupled to a solid support via an intervening linker. The linker may comprise at least one functional group coupled to a linking moiety. The linking moiety may comprise any molecule capable of being coupled to a functional group. For example, the linking moiety may include any of an alkyl, an alkenyl or an alkynyl group. The linking moiety may comprise a carbon chain ranging from 1 to 30 carbon atoms. In some embodiments the linker may be comprised of more than 30 carbon atoms. The linking moiety may comprise at least one hetero-atom such as nitrogen, oxygen and sulfur. The linking moiety may be comprised of a branched chain, an unbranched chain or a cyclic chain. The linking moiety may be substituted with two or more functional groups.

Choosing the appropriate buffer conditions for coupling a protein ligand to a solid support is well within the capability of the skilled artisan. Suitable buffers include any non-amine containing buffer such as carbonate, bicarbonate, sulfate, phosphate and acetate buffers.

When associative chemistry is used, salt concentration of the buffer will depend on the associative group used. For example, the salt concentration may be in the range of 5 nM-100 mM. Where a charged species is used, the salt concentration may be at least 5 nM but less than 0.1M, at least 5 nM but less than 0.01M, at least 5 nM but less than 0.001M. In certain embodiments, the salt concentration may be 0.01M. Where a hydrophobic species is used a high salt concentration is usually desirable. Thus the salt concentration may be greater than 0.001 M, greater than 0.01 M, or greater than 0.1 M.

In some embodiments, when associative chemistry is used, the reaction is performed at a temperature ranging from 0° C. to 99° C. In certain embodiments the reaction method is practiced at a temperature less than 60° C., less than 40° C., less than 20° C., or less than 10° C. In some embodiments the method of the invention is practiced at a temperature of about 4° C. In other embodiments the method of the invention is practiced at a temperature of 20° C.

In other embodiments, the N-intein fusion protein may be combined with various modifiers (membranes, polymeric surfaces, fluorescent or other detection labels) in combination with appropriate cross-linking or condensing chemicals to form a covalent adduct that includes the N-intein fusion protein and the modifier.

IV. Methods of Using Intein-Based Fusion Proteins of the Invention

The fusion proteins described herein containing N-intein polypeptides and N-intein solubilization partners, and the affinity chromatography matrices comprising such fusion proteins, have utility, inter alia, in affinity purification methods, methods of screening for active split intein complexes suitable for use in affinity purification methods, and peptidic cleavage and ligation methods, as described further herein.

Accordingly, the present invention, in certain embodiments, relates to a method of affinity purifying a target molecule in a sample. In one aspect of this embodiment, the method comprises a) providing a sample containing a first fusion protein comprising a C-intein polypeptide joined to a target molecule by a peptide bond; b) contacting the sample with an affinity chromatography matrix that comprises a second fusion protein, wherein the second fusion protein comprises an N-intein polypeptide joined by a peptide bond to an N-intein solubilization partner that promotes solubility of the N-intein polypeptide, under conditions in which the C-intein polypeptide in the first fusion protein selectively binds to the N-intein polypeptide in the second fusion protein to form an intein complex that is inactive; c) washing the affinity chromatography matrix containing the inactive intein complex to remove unbound contaminants; d) exposing the intein complex to conditions under which the intein complex is active and cleaves the target molecule from the C-intein polypeptide; and e) recovering the cleaved target molecule.

The fusion protein comprising an N-intein polypeptide joined to an N-intein solubilization partner can be any of the N-intein fusion proteins described elsewhere herein.

The sample containing the fusion protein comprising a C-intein polypeptide joined to a target molecule can be any suitable sample (e.g., biological sample). In one embodiment, the sample is a crude protein preparation or mixture (e.g., a cell extract).

The target molecule can be any biomolecule of interest. By way of example, biomolecules of interest can include proteins and biomolecular assemblies (e.g., produced by recombinant DNA technology), such as, e.g., hormones (e.g. insulin, human growth hormone, erythropoietin, interferons, granulocyte colony stimulating factor, tissue plasminogen activator), monoclonal antibodies (mAbs) and mAb-derivatives (e.g., bi-specific mAbs, Fabs, scFvs, shark and camelid antibodies), scaffold-derived therapeutics (e.g., DARPins, Affibodies, anticalins), therapeutic enzymes (e.g., alpha galactosidase A, alpha-L-iduronidase, N-acetylgalactosamine-4-sulfatase, glucocerebrosidase), toxins (e.g. botulinum, CRM 197, ricin), recombinant vaccines (e.g., anthrax, diphtheria, tetanus, pneumonia, hepatitis B virus, human papilloma virus), virus-like particles (e.g., hepatitis B, human papilloma, influenza, parvovirus, Norwalk viruses), as well as industrial enzymes (e.g., papain, bromelain, trypsin, proteinase K, BENZONASE™ enzyme, DENERASE™ enzyme, urease, pepsin, etc.) and diagnostic reagents (e.g., glucose and lactate dehydrogenase, DNA polymerases, alkaline phosphatase, horseradish peroxidase, restriction enzymes, hybridoma-derived antibodies, etc.). In a particular embodiment, the target molecule is an antibody (e.g., a monoclonal antibody) to a therapeutic target.

Depending on the particular intein used (e.g., Synechocystis species (Ssp) DnaB, Nostoc punctiforme (Npu) DnaE, GP41-1), loading, washing, cleavage, and elution conditions differ significantly. Nonetheless, appropriate loading, washing, cleavage, and elution conditions for a particular intein can be readily determined by persons of ordinary skill in the art. Suitable conditions (e.g., concentration of chaotropic and reducing/oxidizing agents, metal ions (e.g., zinc, calcium, strontium, magnesium, manganese), volume excluding agents (e.g. PEG, PVP, dextran), detergents, salts, temperature, and pH) for particular inteins include, but are not limited to, conditions described herein below. For the GP41-1 intein in particular, it is known that activity is relatively unaffected by pH in the range of 6-10 (Carvajal-Vallejos P., et al., *J. Biol. Chem.* 287: 28686-28696 (2012)).

Conditions under which the C-intein polypeptide in the first fusion protein selectively binds to the N-intein polypeptide in the second fusion protein to form a catalytically-inactive intein complex can be determined by one of ordinary skill in the art for a given intein. In general, for industrial scale process, changing temperature during a chromatographic separation is viewed as impractical since the change would result in a lengthy equilibration step to ensure that the column and packing temperature is uniform throughout. Exemplary binding conditions include a) a temperature in the range of about 4-25° C., and a buffer comprising 50 mM Tris/HCl, 300 mM NaCl, 1 mM EDTA, 10% (v/v) glycerol, 2 mM DTT, pH=7 (e.g., for GP41-1, see Carvajal-Vallejos P., et al., *J. Biol. Chem.* 287: 28686-28696 (2012)); b) a temperature in the range of about 4-25° C., and a buffer comprising 50 mM NaAc, 0.5 M NaCl, pH=5 (e.g., for DnaB intein, see Lu W., et al., *J. Chrom.* A, 1218: 2553-2560 (2011)); and c) a temperature in the range of about 4-25° C., and a buffer comprising 0.5 M NaCl, 10 mM Tris-HCl, 0.5 mm zinc chloride, pH=8 (e.g., for Npu DnaE, see Guan D., et al., *Biotech. Bioeng.* 110:2471-2481 (2013)).

Similarly, conditions that promote catalytic activity of the intein complex can vary depending on the inteins used and can be determined by one of ordinary skill in the art. Exemplary conditions for promoting catalytic intein activity include a) a buffer comprising 50 mM Tris-HCl, pH=7.0, 300 mM NaCl, 1 mM EDTA; b) a buffer comprising 0.3 M L-arginine, 5 mM EDTA, 50 mM phosphate buffer, pH=6.5; and c) a buffer comprising 0.5 M NaCl, 10 mM Tris-HCl, 50 mM DTT, pH=8.0.

In an aspect of this embodiment, the method can further comprise cleaning, regenerating and/or storing the affinity chromatography matrices of the invention. Typically, an affinity chromatography matrix can be cleaned under alkaline or acidic conditions, depending on the composition of the matrix. Suitable conditions for cleaning, regenerating, restoring and/or storing an affinity matrix can be determined by one of ordinary skill in the art.

An exemplary affinity purification method of the invention is provided in FIG. 1 and Example 10 disclosed herein.

In yet another embodiment, the invention relates to a method of screening for a catalytically-active intein complex that is suitable for use in affinity purification. In an aspect of this embodiment, the method comprises a) contacting a first fusion protein that comprises a C-intein polypeptide joined to a target molecule by a peptide bond with a second fusion protein that comprises an N-intein polypeptide joined to an N-intein solubilization partner by a peptide bond, under conditions in which the C-intein polypeptide in the first fusion protein selectively binds to the N-intein polypeptide in the second fusion protein to form an intein complex; and b) determining whether the target molecule is cleaved from the C-intein polypeptide under conditions which support intein activity, wherein the presence of the cleaved target molecule is indicative of a catalytically-active intein complex.

The N- and C-inteins employed in the method of this embodiment can be any pair of complementary split inteins, such as, for example, the split intein pairs disclosed herein (e.g., GP41-1 N-intein and C-inteins).

Conditions under which the C-intein polypeptide in the first fusion protein selectively binds to the N-intein polypeptide in the second fusion protein to form a catalytically-inactive intein complex can vary depending on the inteins used and can be determined by one of ordinary skill in the art. Exemplary binding conditions include a) a temperature in the range of about 4-25° C., and a buffer comprising 100 mM Tris-HCl, 25 mM NaCl, 0.1 mM zinc chloride, pH=9; b) a temperature in the range of about 4-25° C., and a buffer comprising 50 mM NaAc, 0.5 M NaCl, pH=5; and c) a temperature in the range of about 4-25° C., and a buffer comprising 0.5 M NaCl, 10 mM Tris-HCl, pH=8.

The target molecule can be any suitable target molecule, including, but not limited to, any of the target molecules disclosed herein.

EXAMPLES

Example 1

Selection of Characterization of Candidate Solubilization Partners for the GP41-1 N-Intein Using the set of the 4000+ known Escherichia proteins as a starting point, seven solubilization partners (see Table 2, SEQ ID NOs:11-15, 19, 20) were selected for testing using the following criteria:

(1) selected proteins lacked cysteine residues;

(2) selected proteins were predicted in silico to be soluble when overexpressed in *E. Coli;*

(3) selected proteins had a molecular weight less than 11 kDa;

(4) selected proteins were predicted in silico or known not to be secreted;

(5) where information concerning protein interactions was available, selected proteins were monomeric rather than multimeric;

(6) where information concerning protein function was available, selected proteins were not regulatory or toxic in nature, meaning that they were not involved in the control of major cellular pathways or likely to cause the death of *E. Coli* overexpressing them (e.g. nucleases, polymerases, etc.); and (7) proteins that had known NMR or X-ray crystallographic structures were favored.

Table 3 provides physical properties (molecular weight (mw), isoelectric pH (pI), probability of soluble expression in *E. coli*, whether protein is predicted to be secreted in *E. coli*, the GRand AVerage hYdrophobicity (GRAVY), and the Aliphatic Index (AI)) for inteins and solubilization partners assessed in this study, which were computed using publicly-available algorithms. All of the physical parameters, with the exception of the probability of solubility upon overexpression in *E. coli* and prediction of likelihood of secretion, were calculated using the online ProtParam tool (web.expasy.org/tools/protparam/) that is part of the SwissProt ExPASy suite of bio informatics tools. The molecular weight is given in Daltons. The pI for each protein is the pH value at which the protein has no net charge. Isoelectric point (pI) is a pH in which net charge of protein is zero. In case of proteins isoelectric point mostly depends on seven charged amino acids: glutamate (δ-carboxyl group), aspartate (ß-carboxyl group), cysteine (thiol group), tyrosine (phenol group), histidine (imidazole side chains), lysine (ε-ammonium group) and arginine (guanidinium group). Additionally, one should take into account charge of protein terminal groups (NH2 i COOH). Each of them has its unique acid dissociation constant referred to as pK. Moreover, net charge of the protein is in tight relation with the solution (buffer) pH. Keeping in mind this we can use Henderson-Hasselbach equation to calculate protein charge in certain pH:

| Amino acid | NH2 | COOH | C | D | E | H | K | R | Y |
|---|---|---|---|---|---|---|---|---|---|
| pKa (wikipedia) | 8.2 | 3.65 | 8.18 | 3.9 | 4.07 | 6.04 | 10.54 | 12.48 | 10.46 |

The Grand average of hydropathicity (GRAVY) (Kyte J and Doolittle R F., J. Mol. Biol. 157:105, 1982) of a linear polypeptide sequence is calculated as the sum of hydropathy values of all amino acids, divided by the number of residues in the sequence. Increasing positive score indicates greater hydrophobicity. The calculation is based on the Kyte-Doolittle scale. GRAVY is s simple method for displaying the hydropathic character of a protein.

| | |
|---|---|
| Alanine | 1.8 |
| Arginine | −4.5 |
| Asparagine | −3.5 |
| Aspartic acid | −3.5 |
| Cysteine | 2.5 |
| Glutamine | −3.5 |
| Glutamic acid | −3.5 |
| Glycine | −0.4 |
| Histidine | −3.2 |
| Isoleucine | 4.5 |
| Leucine | 3.8 |
| Lysine | −3.9 |
| Methionine | 1.9 |
| Phenylalanine | 2.8 |
| Proline | −1.6 |
| Serine | −0.8 |
| Threonine | −0.7 |

-continued

| | |
|---|---|
| Tryptophan | −0.9 |
| Tyrosine | −1.3 |
| Valine | 4.2 |

The Aliphatic Index (Ikai, A J., J. Biochem. 88:1895, 1980) of a protein is defined as the relative volume occupied by aliphatic side chains (alanine, valine, isoleucine, and leucine). It may be regarded as a positive factor for the increase of thermostability of globular proteins. The aliphatic index of a protein is calculated according to the following formula: Aliphatic index=X(Ala)+a*X(Val)+b*(X(Ile)+X(Leu)). *The coefficients a and b are the relative volume of valine side chain (a=2.9) and of Leu/Ile side chains (b=3.9) to the side chain of alanine. The probability of generating a soluble product upon overexpression in *E. Coli* can also be calculated using the algorithm of Wilkinson and Harrison (Wilkinson D L and Harrison R G., Bio/Technology, 9: 443, 1991). Other available algorithms do not necessarily give similar results.

The prediction of whether the protein contains a functional secretion signal was performed using the SignalP 4.1 algorithm available from the Center for Biological Sequence Analysis at the Technical University of Denmark (genome.cbs.dtu.dk/services/SignalP/).

TABLE 3

Physical Parameters Measured for Inteins and N-intein Solubilization Partners Used in this Study

| PROTEIN | MOLECULAR WEIGHT (D) | PI | PROBABILITY SOLUBILITY IN *E. COLI* | SECRETED | GRAVY | ALIPHATIC INDEX |
|---|---|---|---|---|---|---|
| SOLUBILIZATION PARTNER 46 | 5639.4 | 5.8 | 74 | NO | −0.086 | 95.7 |
| SOLUBILIZATION PARTNER 206 | 8799.8 | 5.6 | 97 | NO | −0.636 | 93.9 |
| SOLUBILIZATION PARTNER 246 | 9385.6 | 5.4 | 84 | NO | −0.38 | 89.3 |
| SOLUBILIZATION PARTNER 51 | 6024.8 | 4.5 | 98 | NO | −0.391 | 117.7 |
| SOLUBILIZATION PARTNER 138 | 8325.2 | 5.4 | 69 | NO | −1.526 | 48.0 |
| SOLUBILIZATION PARTNER 138_GKL22GCKL | 8428.3 | 5.4 | 60 | NO | −1.469 | 47.3 |
| SOLUBILIZATION PARTNER 138_GYQ48GCYQ | 8428.3 | 5.4 | 60 | NO | −1.469 | 47.3 |
| SOLUBILIZATION PARTNER 138_GYQ48GCGYQ | 8485.4 | 5.4 | 60 | NO | −1.454 | 46.6 |
| SOLUBILIZATION PARTNER 342 | 10000 | 4.3 | 98 | NO | −0.148 | 93.4 |
| SOLUBILIZATION PARTNER 368 | 10750.2 | 6.5 | 72 | NO | −0.398 | 95.5 |
| GP41-1 N-INTEIN VARIANT NINTAA_CC | 10589.1 | 5.8 | 21 | NO | −0.44 | 80.1 |
| GP41-1 C-INTEIN (CINT) | 4916.7 | 5.1 | 86 | NO | −0.312 | 111.4 |
| GP41-1 C-INTEIN FUSION WITH THIOREDOXIN (CINT_TRX) | 17528.1 | 5.5 | 78 | NO | −0.189 | 101.35 |
| SOLUBILIZATION PARTNER A | 20504.9 | 4.6 | 34 | NO | −0.14 | 91.5 |
| SOLUBILIZATION PARTNER B | 7597.6 | 5.6 | 51 | NO | −0.606 | 96.0 |
| SOLUBILIZATION PARTNER C | 1281.5 | 5.4 | 94 | NO | 0.127 | 123.6 |
| SOLUBILIZATION PARTNER D | 37389.1 | 6.3 | 42 | NO | −0.388 | 77.9 |
| SOLUBILIZATION PARTNER E | 12740.2 | 5.8 | 41 | NO | −0.299 | 60.4 |
| SOLUBILIZATION PARTNER F | 43387.6 | 5.5 | 40 | NO | −0.251 | 85.4 |
| SOLUBILIZATION PARTNER G | 12629.4 | 5.7 | 74 | NO | −0.143 | 97.6 |
| SOLUBILIZATION PARTNER H | 54870.9 | 4.5 | 95 | NO | −0.278 | 98.0 |

Example 2

Creation of E. Coli Protein Expression Constructs

Plasmid constructs bearing the coding sequence for the potential solubilization partners 46, 206, and 246 were fused to the coding sequence for NINTΔA_CC either via the amino or carboxy terminal amino acid of NINTΔA_CC and inserted into a version of pJ414 from DNA2.0. These constructs were transformed into competent BL21 DE3 E. Coli cells using conventional methods and ampicillin resistant colonies were isolated. Production of proteins of the expected size was confirmed using SDS polyacrylamide electrophoresis (SDS PAGE).

Transformants of each of the 6 constructs were cultured in 2 mL LB containing 100 ug ampicillin/mL (LB+Amp) from a glycerol stock of BL21 DE3 E. Coli cells transformed with the corresponding construct. This pre-inoculum was grown overnight at 37° C. and 250 rpm and used to inoculate 200 mL of LB+Amp (1% inoculum). The culture was incubated at 37° C. and 250 rpm to an $OD_{600}$ between 0.5-0.6. Protein expression was induced by the addition of 0.4 mM IPTG. Temperature was decreased to 30° C. and the culture was incubated at this temperature and 250 rpm for 5 hours. After that time, cells were harvested by centrifugation (4500 g, 25 min, 4° C.), supernatant was discarded and the cell pellet was kept at −80° C. for further protein purification.

The coding region for the test substrate protein CINT_TRX was cloned into pSABAD92A (GenBank accession HM070247) and transformed into competent BL21 DE3 cells. Successful transformants were isolated on Luria broth plus 50 ug/ml carbenecillin (LB+C). Production of proteins of the expected size was confirmed using SDS PAGE. Glycerol stocks of each of the three BL21 clones/construct are stored at −80° C.

A small amount of frozen BL21 glycerol stocks was used to inoculate a 5 ml culture in LB+C at 37° C., 250 rpm. The following day, 0.1 ml of the overnight grown culture is used to inoculate 10 ml LB+C and this culture is grown at 37° C., 250 rpm to an $OD_{600}$ of 0.6-0.9. Cultures were induced with 0.02% arabinose at 28° C., 250 rpm for 5 hours. After induction, cells were harvested by centrifugation (4500 g, 25 min, 4° C.), supernatant was discarded and the cell pellet was kept at −80° C. for further protein purification.

Example 3

Determination of Soluble vs Insoluble Ratio and Total Amount of Expressed Proteins In order to determine expression yields and soluble:insoluble ratio for each construct, aliquots of grown cultures corresponding to equivalent biomasses, cultured as indicated above, were centrifuged at 5000 g, 15 min, 4° C. After discarding culture supernatant, cells were resuspended in 200 uL of a solubilization buffer consisting of 50 mM Tris pH 8, 300 mM NaCl, 0.5% Triton X-100. Cells were broken by sonication (10 burst×3, Branson 250 Sonifier, with time between each series to allow sample cooling). To separate soluble and insoluble fraction, samples were centrifuged at 16000 g and 4° C. for 10 min. Soluble fractions were removed to a separate tube while insoluble fractions were resuspended in 200 μL of the same solubilization buffer by sonication (using the same parameters as in the previous sonication).

Recombinant proteins in cell lysates were quantified after SDS PAGE gel after Coomassie staining using densitometric analysis of the using a curve of quantified BSA as a reference. Three different sample volumes per clone were loaded along with the BSA standard curve (6 points from 0.2 to 1.2 ug). Intensities of protein bands were determined by densitometry using the "Quantity One" (Biorad) software. A correction factor is applied for each protein considering the BSA/recombinant protein molecular weight ratio.

Concentrations for purified proteins were determined using calculated extinction coefficients and their absorbance calculated at 280 nm.

Example 4

Purification of Expressed Proteins

To purify the C-intein fusion protein CINT_TRX used as cleavage substrate throughout, E. Coli cells expressing the protein were resuspended in buffer containing 50 mM Tris-HCl, pH=8.0, 300 mM NaCl, 0.5× CelLytic B (Sigma-Aldrich), and 20 mM imidazole. Cells were sonicated on ice for 20 min with a 30% pulsed activity cycle (Branson 250 Sonifier) and centrifuged for 30 min at 34500 g at 4° C. Soluble C-intein fusion was purified from the supernatant on His-Trap HP (GE Healthcare) columns, following manufacturer's instructions. Eluted fractions containing the purified C-intein fusion proteins were pooled, dialyzed against cleavage buffer (50 mM Tris-HCl, pH=7.0, 300 mM NaCl, 1 mM EDTA, 10% (v/v) glycerol; CB) in the presence of 2 mM DTT, and stored in aliquots at −80° C.

N-intein fusions were purified under native conditions from E. Coli cells harboring the expression constructs. Cell pellets were resuspended in buffer containing 100 mM Tris-HCl, pH=8.0, 150 mM NaCl, and 1 mM EDTA. Cells were then sonicated on ice for 20 min with a 30% pulsed activity cycle (Branson 250 Sonifier) and centrifuged for 30 min at 34500 g at 4° C. The soluble fraction of the N-intein fusion was purified by chromatography on His-Trap HP columns as described above. Eluted fractions containing the purified protein were pooled, dialyzed against CB in the presence of 2 mM DTT and stored in aliquots at −80° C.

Example 5

Determination of Cleavage Kinetics for Expressed Proteins

In vitro reactions were performed as previously described (Carvajal-Vallejos P., et al., J. Biol. Chem. 287: 28686, 2012). In brief, purified N- and C-fusion proteins were briefly pre-incubated separately in the corresponding test conditions. Cleavage reaction were initiated by mixing complementary N- and C-intein fusion proteins in cleavage buffer at equimolar concentrations of 5 μM, and incubated at 25° C. and 37° C. For the experiments related to this invention, the cleavage partner was always CINT_TRX. Aliquots are removed at specific time intervals, and the reaction was stopped by the addition of SDS PAGE buffer containing 8% SDS (w/v) and 20% β-mercaptoethanol (v/v), followed by 5 minutes of boiling. Reactions products were quantified by SDS PAGE (4-12% Bis-Tris gels from Novex, Invitrogen, Carlsbad, US), followed by Coomassie Brilliant Blue (Sigma) staining. Relative intensities of protein bands were determined densitometrically using the Quantity One (BioRad) program. The different cleavage products were normalized according to their corresponding molecular weight. The percentage of protein cleavage was calculated from the ratio of the cleaved products and the intein-tagged precursor CINT_TRX. Constant rates (kobs) were determined using the GraFit software (Erithacus, Surrey, UK), by fitting the data to the equation $P=P_0(1-e^{-kt})$, where P is the amount of cleaved C-intein fusion product formed at time t, $P_0$ is the maximum amount of cleaved product that can be obtained (yield), e is Euler's constant, and k is the observed rate. All reactions were treated as irreversible, pre-steady state, and first-order processes under the assumption that, after rapid association of the two complementary intein fragments, cleavage of the C-intein fusion protein proceeds like a mono-molecular reaction.

Example 6

Figure 2:
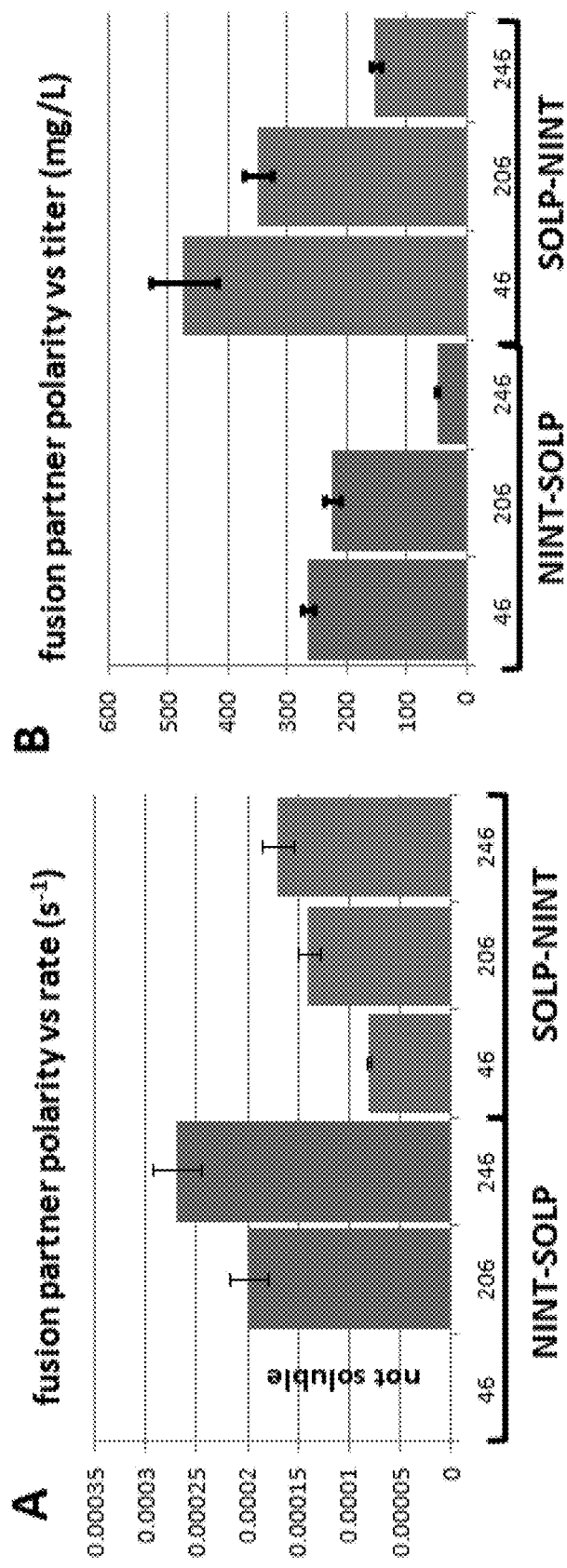
FIG. 2A is a graph depicting the effect of fusion polarity on catalytic activity (rate of cleavage) for three candidate N-intein solubilization partners (46, 206, 246; see Table 2) that were fused to either the N-terminus (SOLP-NINT) or C-terminus (NINT-SOLP) of the GP41-1 N-intein.
FIG. 2B is a graph depicting the effect of fusion polarity on protein expression in *E. Coli* for three candidate N-intein solubilization partners (46, 206, 246) that were fused to either the N-terminus (SOLP-NINT) or C-terminus (NINT-SOLP) of the GP41-1 N-intein.

Determination of Optimal Placement and Properties for NINT Solubilization Partners NINTΔA_CC fusions to potential solubilization partners were created in both possible orientations (i.e. fused either to the N- or C-terminus of NINTΔA_CC) for all solubilization partners. The six resulting constructs were expressed in *E. Coli* and the protein produced was analysed with respect to total amount produced and solubility as previously described. In addition, protein from each construct was purified and the rate of cleavage using purified CINT_TRX as substrate was characterized. The results of this analysis are shown in FIGS. 2A and 2B. While fusion of the solubilization partner to the N-terminus of NINTΔA_CC produces higher amounts of protein in *E. Coli* for all constructs tested that the fusion of the solubilization partner to the C-terminus, the reverse of this trend is seen when cleavage rates are measured. Work published using a different split intein system while these studies were ongoing demonstrated a similar relationship between the location of the solubilization partner and the N-intein and N-intein activity that was explained by referring to known structural information that indicates a greater likelihood of steric interference between extein domains when the fusion is made in the opposite polarity (Guan D, Ramirez M, Chen Z., *Biotechnol Bioeng.* 110:2471, 2013).

Figure 3:
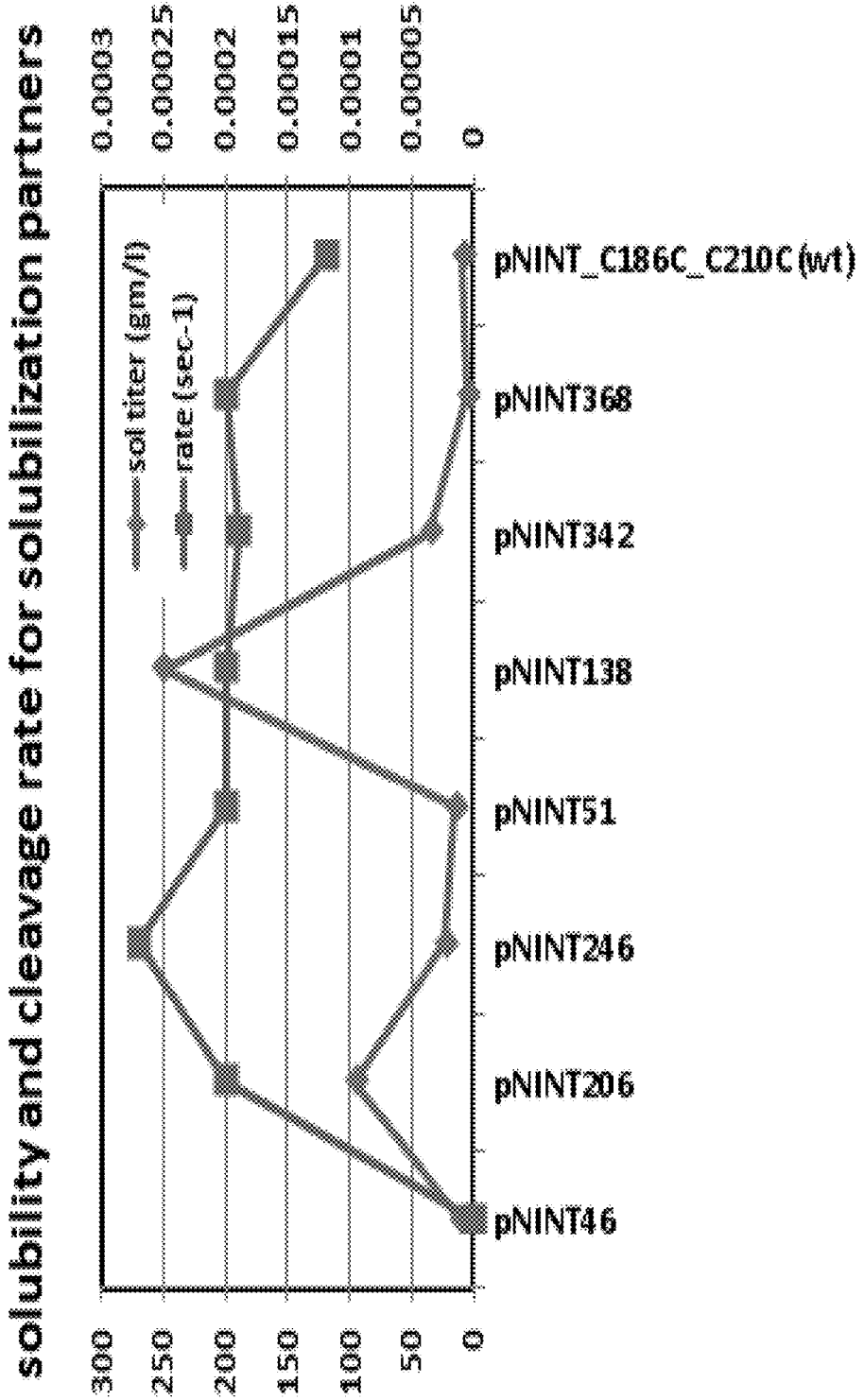
FIG. 3 is a graph depicting substrate cleavage rates and soluble expression titers for seven candidate solubilization partners (46, 206, 246, 51, 138, 342, 368) that were fused to the C-terminus of the GP41-1 N-intein.

This work was extended to include additional solubilization partners 51, 138, 342, and 368 (see Tables 2 and 3) that were distinct from previously characterized solubilization partners in terms of size and isoelectric point (pI). All of these were fused to the carboxyl terminus of NINTΔA_CC as was shown previously with solubilization partners 46, 206, and 246 to yield fusions having the highest catalytic activity. These constructs were expressed in *E. Coli*, purified, and analyzed for cleavage rate as described previously. The results of these analyses are presented in FIG. 3. While the solubilization partner 246 clearly has the highest activity, the best compromise between catalytic activity and soluble expression was observed for solubilization partner 138.

Figure 4:
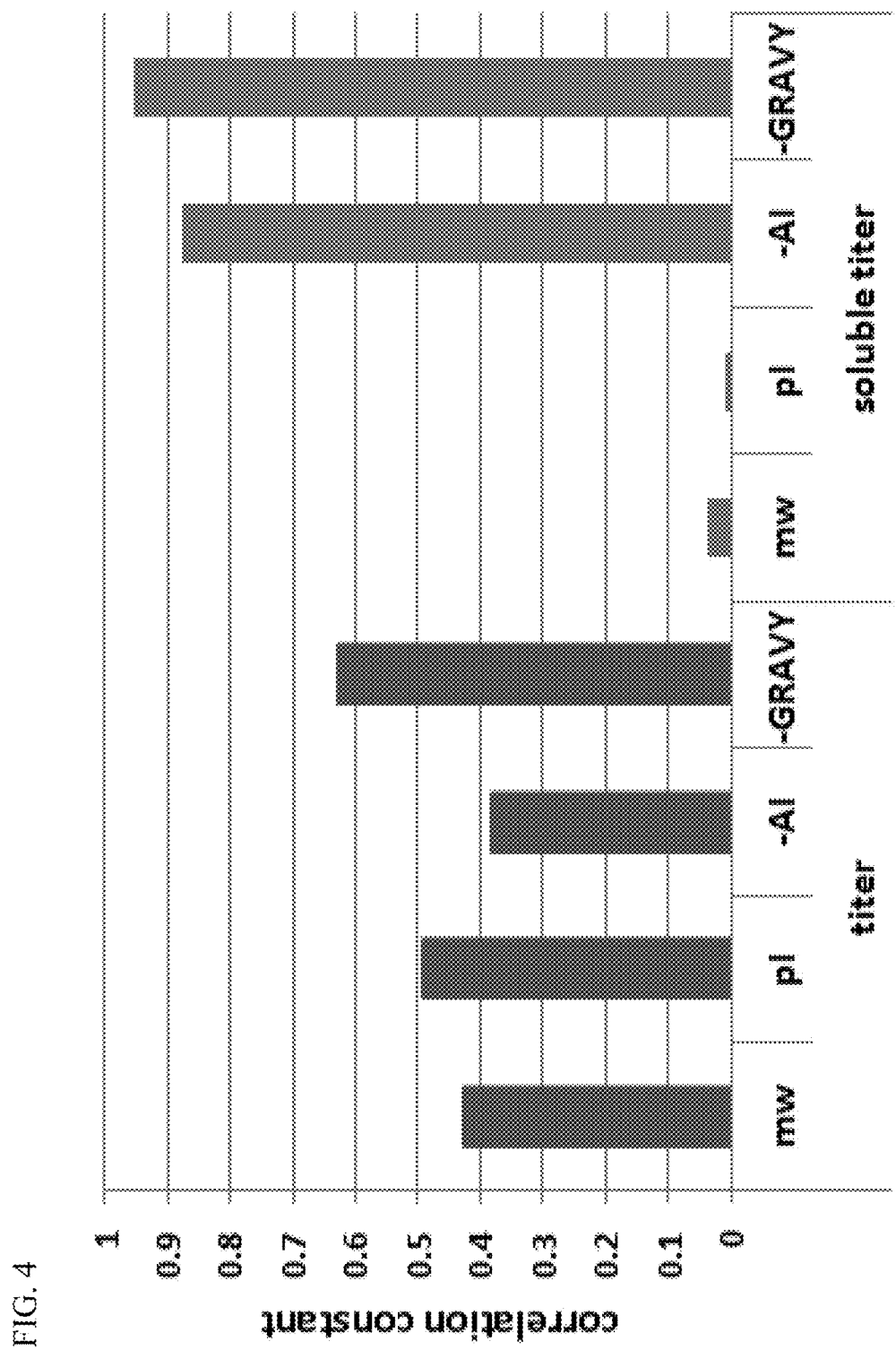
FIG. 4 is a graph depicting the correlation between calculated physical properties of candidate solubilization partners and either total (titer) or soluble (soluble titer) expression in *E. Coli* of fusion proteins containing the solubilization partner fused to the C-terminus of the N-intein. mw: molecular weight; pI: isoelectric point; AI: aliphatic index; GRAVY: grand average of hydropathy.

In order to understand the properties of solubilization partner 138 that make it effective for the solubilization of N-intein during expression in *E. Coli*, the calculated protein parameters for each of the candidate solubilization in Table 3 were correlated to soluble titer in FIG. 4. While none of these parameters correlated strongly with overall expression, both AI and GRAVY values showed a negative correlation with soluble titer.

Example 7

Selection of Amino Acids for Replacement of Cysteine Residues in NINTΔA_CC

The GP41-1 N-intein isolated from natural sources contains three cysteine residues, but one had previously been replaced to give NINTΔA_CC, the parent construct for this invention. The remaining two cysteine residues contained within NINTΔA_CC were targeted for replacement so that a unique, reactive cysteine residue could be introduced into the solubilization domain for subsequent immobilization or other modification.

Figures 5A, 5B:
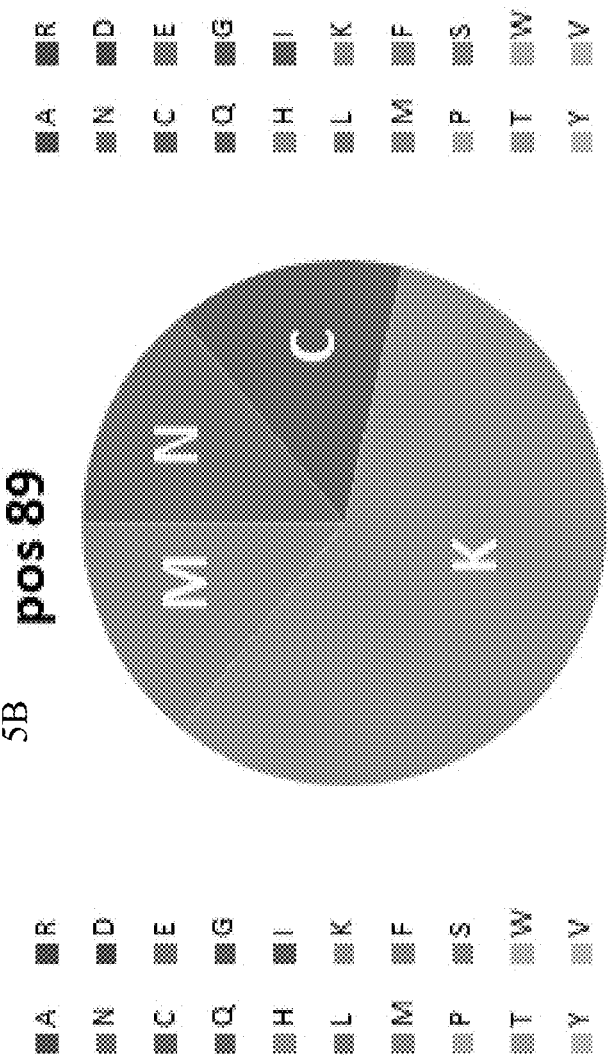
FIG. 5A is a chart showing the frequencies with which particular amino acids are found in roughly one hundred GP41-1 homologs at the residue corresponding to the cysteine at position 65 of the GP41-1 intein.
FIG. 5B is a chart showing the frequencies with which particular amino acids are found in roughly one hundred GP41-1 homologs at the residue corresponding to the cysteine at position 89 of the GP41-1 intein.

To identify amino acids that could be substituted for the two cysteine residues in NINTΔA_CC and still yield a stable and functional intein protein, several phylogenetic analyses were performed in which protein sequences were aligned and naturally occurring amino acid variants at positions 65 and 89 in SEQ ID NO:1 were examined. Replacement of the naturally-occurring internal cysteines in GP41-1 with other amino acids occurring at these positions in similar inteins would be expected to yield functional and/or stable GP41-1 variant proteins as natural selection has allowed these variants to persist in nature. When such an analysis is performed with N-inteins of the GP41 intein class (1, 2, 3, 4, 5, 6; Dassa B., et al., *Nucl. Acids Res.*, 37:2560-2573 (2009)), the two cysteine residues at positions 65 and 89 in SEQ ID NO:1 are found to be highly conserved, suggesting that substituting these cysteines would adversely affect the activity and/or stability of the GP41-1 intein. However, if the analysis is expanded to include slightly more divergent proteins that may or may not have intein function, many proteins are identified that have homology to the phoH gene of the *E Coli* phosphate regulon. Roughly one hundred homologs were obtained from GenBank using the BLAST search tool and aligned with the CLUSTAL algorithm using the freeware tool, BioEdit (Hall T A., *Nucl. Acids. Symp. Ser.* 41:95, 1999). The results of this analysis are shown in FIG. 5, where the position numbering is based on NINTΔA_CC (SEQ ID NO:2). From this analysis, it is clear that threonine and alanine occur frequently at position 65 and that lysine, methionine and asparagines occur frequently at position 89, indicating that substitution of the natural cysteines with these naturally occurring amino acids should yield a stable protein.

Example 8

Screening of NINTΔA_CC Amino Acids Variants for Optimal Properties

Constructs based on NINTΔA_CC (SEQ ID NO:2) containing the amino acid substitutions shown in Table 4 were created, expressed, purified, and characterized for catalytic activity as described previously.

Figure 6:
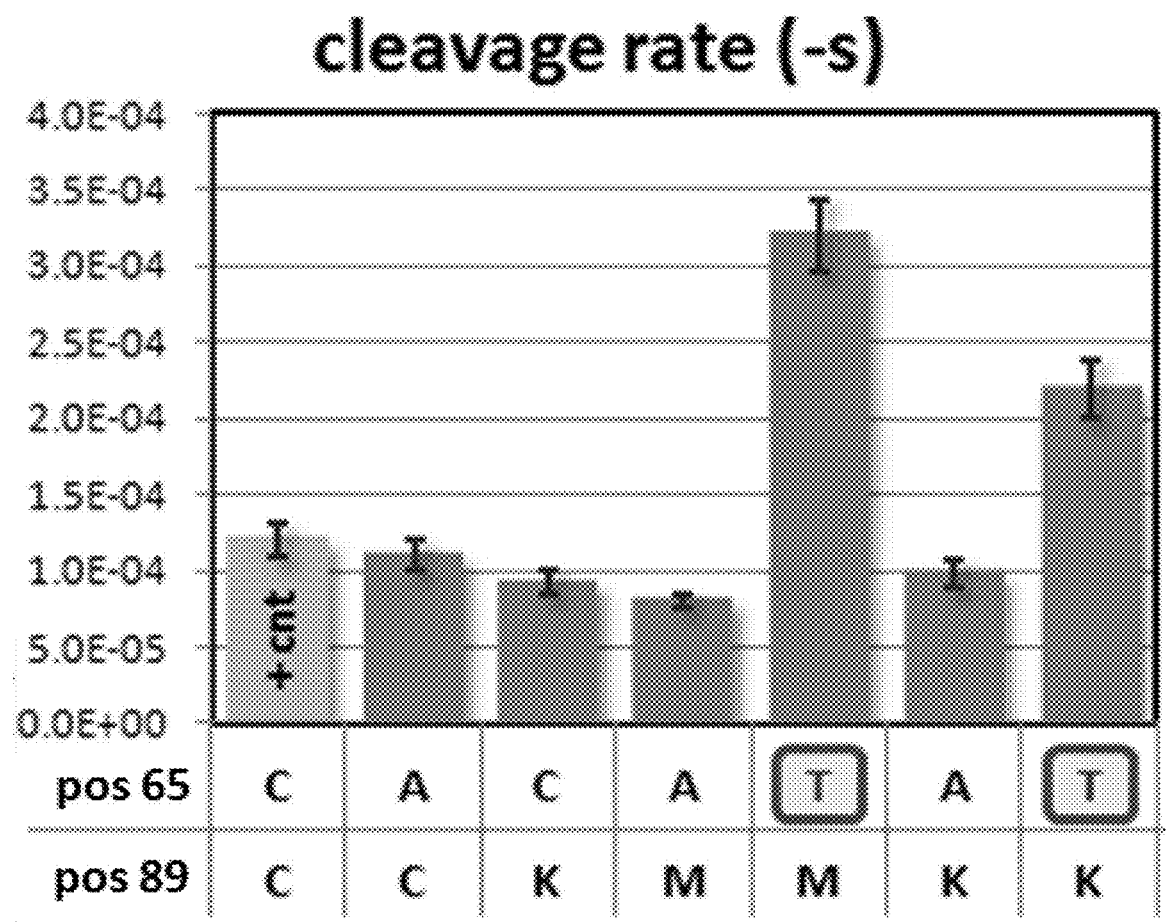
FIG. 6 is a graft depicting the catalytic activities (cleavage rates) of fusion proteins of solubilization partner 138 with the wild type GP41-1 N-intein containing two centrally located, naturally-occurring cysteine residues at positions 65 and 89, or variants of the GP41-1 N-intein that contain amino acid substitutions for one or both of the cysteine residues at positions 65 and 89.

Cleavage rate measurements for N-intein fusions proteins made from each construct are given in FIG. 6. NINTΔA_CC parent (+cnt) is shown at the left for comparison. The amino acids at positions 65 and 89 are shown at the bottom of the figure. A threonine residue at position 65 yields N-intein fusions that have significantly more activity than the parent. Of the constructs tested, the N-intein fusion having a threonine at position 65 and a methionine at position 89 gave a construct with a catalytic rate about three times faster than the parent construct.

TABLE 4

GP41-1 N-intein Variants

| GP41-1 N-intein variant | Sequence |
|---|---|
| NINTΔA_CC (SEQ ID NO: 2) | mtrsgyALDLKTQVQTPQGMKEISNIQVGDLVLSNTGYNEVLNVFPKSKKK<br>SYKITLEDGKEII<u>C</u>SEEHLFPTQTGEMNISGGLKEGM<u>C</u>LYVKEgg |
| NINTΔA_AC (SEQ ID NO: 3) | mtrsgyALDLKTQVQTPQGMKEISNIQVGDLVLSNTGYNEVLNVFPKSKKK<br>SYKITLEDGKEII<u>A</u>SEEHLFPTQTGEMNISGGLKEGM<u>C</u>LYVKEgg |
| NINTΔA_CK (SEQ ID NO: 4) | mtrsgyALDLKTQVQTPQGMKEISNIQVGDLVLSNTGYNEVLNVFPKSKKK<br>SYKITLEDGKEII<u>C</u>SEEHLFPTQTGEMNISGGLKEGM<u>K</u>LYVKEgg |
| NINTΔA_AM (SEQ ID NO: 5) | mtrsgyALDLKTQVQTPQGMKEISNIQVGDLVLSNTGYNEVLNVFPKSKKK<br>SYKITLEDGKEII<u>A</u>SEEHLFPTQTGEMNISGGLKEGM<u>M</u>LYVKEgg |
| NINTΔA_TM (SEQ ID NO: 6) | mtrsgyALDLKTQVQTPQGMKEISNIQVGDLVLSNTGYNEVLNVFPKSKKK<br>SYKITLEDGKEII<u>T</u>SEEHLFPTQTGEMNISGGLKEGM<u>M</u>LYVKEgg |
| NINTΔA_AK (SEQ ID NO: 7) | mtrsgyALDLKTQVQTPQGMKEISNIQVGDLVLSNTGYNEVLNVFPKSKKK<br>SYKITLEDGKEII<u>A</u>SEEHLFPTQTGEMNISGGLKEGM<u>K</u>LYVKEgg |
| NINTΔA_TK (SEQ ID NO: 8) | mtrsgyALDLKTQVQTPQGMKEISNIQVGDLVLSNTGYNEVLNVFPKSKKK<br>SYKITLEDGKEII<u>T</u>SEEHLFPTQTGEMNISGGLKEGM<u>K</u>LYVKEgg |

For SEQ ID Nos: 2-8, non-intein sequences are indicated using lower case text and intein sequences are indicated by upper case text.

Example 9

Strategy for the Introduction of Unique Cysteine Residues into Solubilization Partner 138

Figure 7:
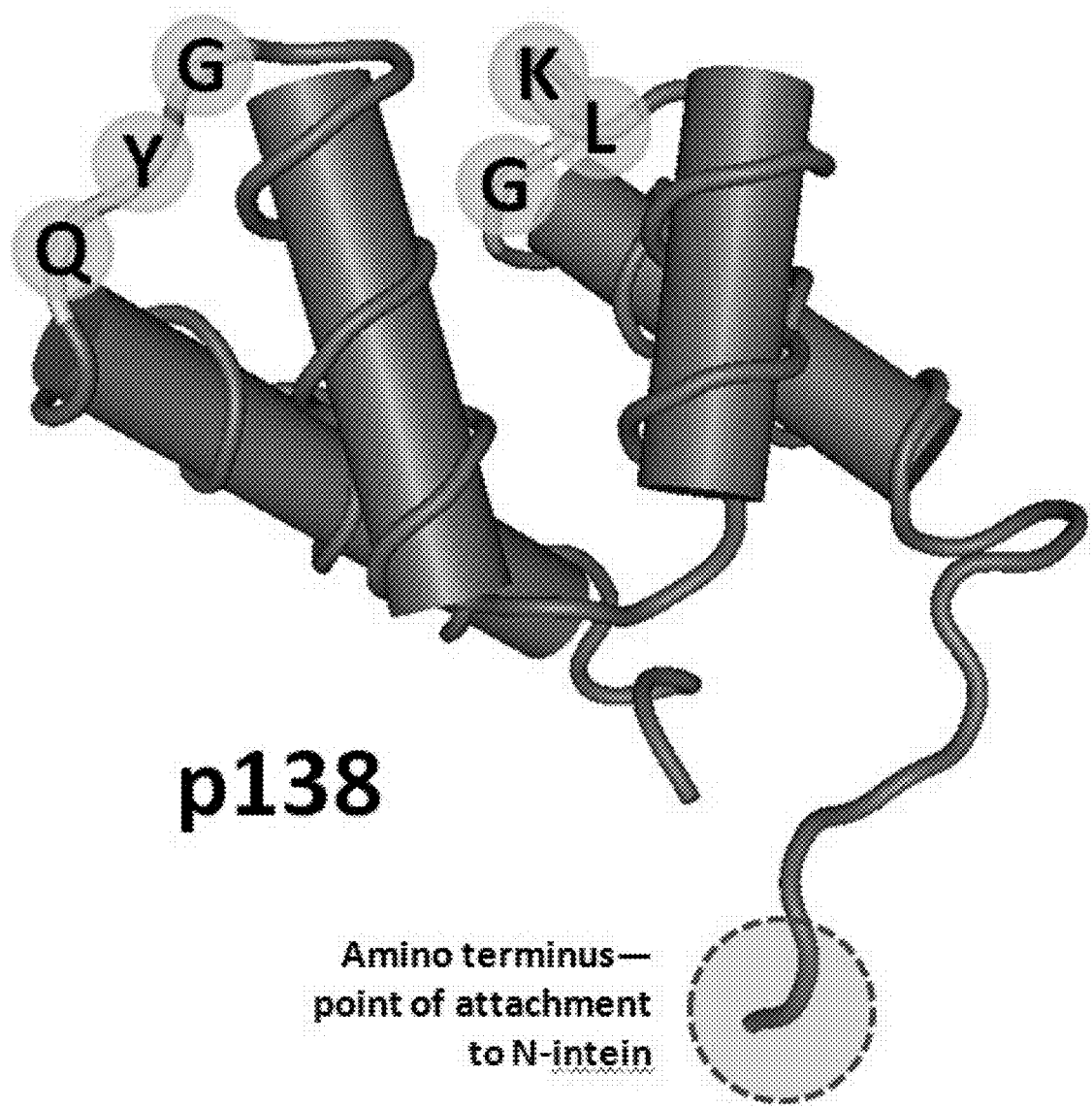
FIG. 7 depicts an NMR solution structure for solubilization partner 138 (Protein Databank structure 1RYK). The protein contains four alpha helix domains, is globular, has a long unstructured coil that forms the connection to the carboxy terminus of the N-intein (circled region; N-intein not shown). The loop regions GKL and GYQ indicated by yellow highlighting were targeted for cysteine residue insertions to create the new versions (GCKL (SEQ ID NO:61), GCYQ (SEQ ID NO:62), and GCGYQ (SEQ ID NO:63)) of solubilization partner 138 (138_GKL22GCKL, 138_GYQ48GCYQ, and 138_GYQ48GCGYQ).

To allow chemical modification of the N-intein fusion protein without diminishing its catalytic activity the site of eventual modification should be as far removed from the active site of the N-intein as possible. In the absence of structural information for solubilization partner 138, a reasonable approach would be to perform a phylogenetic analysis, as described above for the GP41-1 N-intein (see Example 7), determine regions of the protein that display high variability, modify these by the insertion of a cysteine, and then test all of the resulting constructs. There is, however, an NMR solution structure available for solubilization partner 138 (Protein Databank structure 1RYK), which is shown in FIG. 7. The protein contains four alpha helix domains, is globular, has a long unstructured coil that forms the connection to the carboxy terminus of the N-intein (circled region; N-intein not shown). The loop regions GKL and GYQ indicated by yellow highlighting were targeted for cysteine residue insertions to create the new versions (G CKL (SEQ ID NO:61), GCYQ (SEQ ID NO:62), and G CGYQ (SEQ ID NO:63)) of solubilization partner 138 (138_GKL22GCKL (SEQ ID NO:16), 138_GYQ48GCYQ (SEQ ID NO: 17), and 138_GYQ48GCGYQ (SEQ ID NO:18)).

Example 10

Coupling of N-Intein Fusion Protein (Ligand) to Chromatography Resin

A soluble fusion protein containing the solubilization partner 138_GYQ48GCGYQ (SEQ ID NO: 18) fused to the carboxyl-terminus of the GP41-1 variant NINTΔA_TM (SEQ ID NO:6) is expressed from an encoding nucleic acid in E. Coli and is subsequently separated from contaminating cellular proteins using conventional separation methods.

The purified N-intein fusion protein is then coupled to a FRACTOGEL® or ESHMUNO® chromatography resin (EMD Millipore Corporation) through the unique reactive cysteine site in the solubilization partner domain of the fusion protein using standard techniques.

In preparation for activation, 5 ml of wet FRACTOGEL® COO (FG-COO) resin are washed one time with DI water and three times with 150 mM 2-(N-morpholino)ethanesulfonic acid at pH=6.5 (MES buffer) in a Buechner funnel and transferred to a Schott glass bottle. 0.1035 gm 1-ethyl-3-(3-dimethylamino-propyl)carbodiimide (EDC) are dissolved in 3 ml of MES buffer and added to FG-COO. The mixture is incubated for 2 min at room temperature. A solution of 0.1372 gmN-(3-aminopropyl)maleimide trifluoroacetic acid (APM) in 4 ml of MES buffer is added and the mixture is held at room temperature overnight with stirring. pH iss maintained at 6.5 through titration with 1 M NaOH. For storage, the activated resin is resuspended in 150 mM NaCl containing 20% ethanol and stored in a refrigerator. For analysis of functionalization, a 50% v/v solution of activated resin is prepared in 100 mM phosphate buffer containing 150 mM NaCl at pH=7.2 (PO buffer). 0.5 ml of activated FG-COO is mixed with 1 mL of 204 uM cysteine hydrochloride solution in PO buffer and incubated for one hour. A sample of FG-COO that has not been activated with AMP is processed in parallel as a negative control. The resin is then washed extensively with PO buffer, 0.5 M NaCl, and resuspended in 0.5 M NaCl for analysis of free sulfhydryl groups using Ellmann's reagent (5,5'-dithio-bis-(2-nitrobenzoic acid)) and known methods. A ligand density of up to 400 µmol per gram of dry resin is determined using this analysis.

Example 11

Affinity Purification of a Thioredoxin Using Intein Fusion Proteins

Resin containing immobilized N-intein fusion protein prepared according to Example 10 herein is packed into a standard chromatography column and a crude protein mixture containing the CINT_TRX fusion protein (SEQ ID NO: 10), which includes the target molecule thioredoxin fused to the carboxy-terminus of the GP41-1 C-intein, is added to the column containing the immobilized N-intein fusion protein at a temperature in the range of 4-25° C., and using a loading buffer containing 100 mM Tris-HCl, 25 mM NaCl, 0.1 mM zinc chloride, pH=9 to allow strong interaction between the GP41-1 N- and C-intein domains without permitting intein catalysis.

The loaded column is then washed to remove unbound and weakly-bound contaminants using a wash buffer containing detergent (e.g., Triton X100, ND40) or salt (e.g., acetate, phosphate, chloride, sulfate salts of sodium, ammonium, or potassium).

Cleavage and elution of the thioredoxin portion of the C-intein fusion protein is accomplished by the addition of a cleavage buffer (50 mM Tris-HCl, pH=7.0, 300 mM NaCl, 1 mM EDTA). The cleaved thioredoxin is then recovered in the eluate.

TABLE 5

Exemplary Split Inteins and Their Sequences

| Intein | SEQ ID NO: | Sequence |
|---|---|---|
| N-terminal domain of GP41.1 | 29 | CLDLKTQVQT PQGMKEISNI QVGDLVLSNT GYNEVLNVFP KSKKKSYKIT LEDGKEIICS EEHLFPTQTG EMNISGGLKE GMCLYVKE |
| N-terminal domain of GP41.8 | 30 | CLSLDTMVVT NGKAIEIRDV KVGDWLESEC GPVQVTEVLP IIKQPVFEIV LKSGKKIRVS ANHKFPTKDG LKTINSGLKV GDFLRSRA |
| N-terminal domain of NrdJ1 | 31 | CLVGSSEIIT RNYGKTTIKE VVEIFDNDKN IQVLAFNTHT DNIEWAPIKA AQLTRPNAEL VELEINTLHG VKTIRCTPDH PVYTKNRDYV RADELTDDDE LVVAI |
| N-terminal domain of IMPDH1 | 32 | CFVPGTLVNT ENGLKKIEEI KVGDKVFSHT GKLQEVVDTL IFDRDEEIIS INGIDCTKNH EFYVIDKENA NRVNEDNIHL FARWVHAEEL DMKKHLLIEL E |
| N-terminal domain of NrdA-2 | 33 | CLTGDAKIDV LIDNIPISQI SLEEVVNLFN EGKEIYVLSY NIDTKEVEYK EISDAGLISE SAEVLEIIDE ETGQKIVCTP DHKVYTLNRG YVSAKDLKED DELVFS |
| N-terminal domain of Npu DNA-E (Genbank accession ZP_00111398) | 34 | CLSYETEILT VEYGLLPIGK IVEKRIECTV YSVDNNGNIY TQPVAQWHDR GEQEVFEYCL EDGSLIRATK DHKFMTVDGQ MLPIDEIFER ELDLMRVDNL PN |
| N-terminal domain of Ssp DNA-B (Genbank accession Q55418) | 35 | CISGDSLISL ASTGKRVSIK DLLDEKDFEI WAINEQTMKL ESAKVSRVFC TGKKLVYILK TRLGRTIKAT ANHRFLTIDG WKRLDELSLK EHIALPRKLE SSSLQ |
| C-terminal domain of GP41.1 | 9 | MMLKKILKIE ELDERELIDI EVSGNHLFYA NDILTHN |
| C-terminal domain of GP41.8 | 36 | MCEIFENEID WDEIASIEYV GVEETIDINV TNDRLFFANG ILTHN |
| C-terminal domain of NrdJ1 | 37 | MEAKTYIGKL KSRKIVSNED TYDIQTSTHN FFANDILVHN |
| C-terminal domain of IMPDH1 | 38 | MKFKLKEITS IETKHYKGKV HDLTVNQDHS YNVRGTVVHN |
| C-terminal domain of NrdA-2 | 39 | MGLKIIKRES KEPVFDITVK DNSNFFANNI LVHN |
| C-terminal domain of Npu DNA-E (Genbank accession ZP_00111398) | 40 | MIKIATRKYL GKQNVYDIGV ERDHNFALKN GFIASN |

TABLE 5-continued

Exemplary Split Inteins and Their Sequences

| Intein | SEQ ID NO: | Sequence |
|---|---|---|
| C-terminal domain of Ssp DNA-B (Genbank accession Q55418) | 41 | SPEIEKLSQS DIYWDSIVSI TETGVEEVF DLTVPGPHNF VA<u><u>NDIIVHN</u></u> |

Underlined sequences correspond to the N1 boxes of the intein N-terminal domains. Double underlined sequences correspond to the C1 boxes of the intein C-terminal domains (e.g., lacking the first amino acid of the extein).

Additional Exemplary N-Intein Sequences gp 41-2
(SEQ ID NO: 42)
CLDLKTQVQTQQGLKDISNIQVGDLVL gp 41-3
(SEQ ID NO: 43)
CLDLKTQVQTPQGMKEISNIQVGDLVLSNTGYNEVLNVFPKSKKKS gp 41-4
(SEQ ID NO: 44)
CLDLKTQVQTPQGMKEISNIQVGDLVLSNTGYNEVLNVFPKSKKKSYKIT
LEDGKEIICSEEHLFPTQTGEMNISGGLKEGMCLYVKE gp 41-5
(SEQ ID NO: 45)
CLDLKTQVQTPQGMKEISNIQVGDLVLSNTGYNEVLNVFPKSKKKSYKIT
LEDGKEIICSEEHLFPTQTGEMNISGGLKEGMCLYVKE gp 41-6
(SEQ ID NO: 46)
SYKITLEDGKEIICSEEHLFPTQNGEVNIKGGLKEGMCLYVKE gp 41-7
(SEQ ID NO: 47)
MMLKKILKIEELDERELIDIEVSGNH NrdA-1
(SEQ ID NO: 48)
CVAGDTKIKIKYPESVGDQYGTWYWNVLEKEIQIEDLEDYIIMRECEIYD
SNAPQIEVLSYNIETGEQEWKPITAFAQTSPKAKVMKITDEESGKSIVVT
PEHQVFTKNRGYVMAKDLIETDEPIIVNKDMNF NrdA-4
(SEQ ID NO: 49)
CLAGDTTVTVLEGDIVFEMTLENLVSLYKNVFSVSVLSFNPETQKQEFKP
VTNAALMNPESKVLKITDSDTGKSIVCTPDHKVFTKNRGYVIASELNAED
ILEIK NrdA-5
(SEQ ID NO: 50)
HTETVRRVGTITAFAQTSPKSKVMKITDEESGNSIVVTPEEIKVFTKNRG
YVMAKNLVETDELVIN NrdA-6
(SEQ ID NO: 51)
YVCSRDDTTGFKLICTPDHMIYTKNRGYIMAKYLKEDDELLINEIHLPT NrdJ-1
(SEQ ID NO: 52)
CLVGSSEIITRNYGKTTIKEVVEIFDNDKNIQVLAFNTHTDNIEWAPIKA
AQLTRPNAELVELEIDTLHGVKTIRCTPDHPVYTKNRGYVRADELTDDDE
LVVAI NrdJ-2
(SEQ ID NO: 53)
CLVGSSEIITRNYGKTTIKEVVEIFDNDKNIQVLAFNTHTDNIEWAPIKA
AQLTRPNAELVELEINTLHGVKTIRCTPDHPVYTKNRDYVRADELTDDDE
LVVAI Additional Exemplary C-intein Sequences gp 41-9
(SEQ ID NO: 54)
MIMKNRERFITEKILNIEEIDDDLTVDIGMDNEDHYFVANDILTHNT IMPDH-2
(SEQ ID NO: 55)
MKFTLEPITKIDSYEVTAEPVYDIEVENDHSFCVeNGFVVHNS

IMPDH-3
(SEQ ID NO: 56)
MKFKLVEITSKETFNYSGQ-VHDLTVEDDHSYSI-NNIVVHNS,

NrdA-3
(SEQ ID NO: 57)
MLKIEYLEEEIPVYDITVEETHNFFANDILIHNC,

NrdA-5
(SEQ ID NO: 58)
MLKIEYLEEEIPVYDITVEGTHNLAYSL,

NrdA-6
(SEQ ID NO: 59)
MGIKIRKLEQNRVYDIKVEKIIIFCNNILVHNC,
and

NrdJ-1
(SEQ ID NO: 60)
MEAKTYIGKLKSRKIVSNEDTYDIQTSTHNFFANDILVHNS.

The relevant teachings of all patents, published applications and references cited herein are incorporated by reference in their entirety.

Unless otherwise indicated, all numbers expressing quantities of ingredients, expression conditions, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

While this invention has been particularly shown and described with references to example embodiments thereof, it will be understood by those skilled in the art that various changes in form and details may be made therein without departing from the scope of the invention encompassed by the appended claims.

What is claimed is:

1. A soluble fusion protein comprising an N-intein polypeptide capable of forming an active intein complex by associating with a second fusion protein comprising a C-intein polypeptide, and at least one cysteine of the N-intein is substituted with an amino acid selected from the group consisting of: threonine, lysine, asparagine, serine, methionine, and tyrosine, wherein the N-intein polypeptide is covalently attached to a solid support.

2. The N-intein polypeptide of claim 1, wherein the solid support is a bead, a hollow fiber, a solid fiber, a pad, a gel, a membrane, a cassette, a column, a chip, a slide, a plate or a monolith.

3. The N-intein polypeptide of claim 1, wherein the solid support is a chromatography resin.

4. A matrix comprising an N-intein polypeptide having at least one cysteine of the N-intein substituted with an amino acid selected from the group consisting of: threonine, lysine, asparagine, serine, methionine, and tyrosine, and attached, by covalent attachment, to a solid support.

5. The matrix of claim 4, wherein the solid support is a chromatography resin.

6. The matrix of claim 5, wherein the chromatography resin includes a hydrophilic polyvinyl ether base.

7. The matrix of claim 4, wherein the solid support is a bead, a hollow fiber, a solid fiber, a pad, a gel, a membrane, a cassette, a column, a chip, a slide, a plate or a monolith.

8. The matrix of claim 7, wherein the solid support is a magnetic bead.

9. The matrix of claim 8, wherein the solid support comprises controlled pore glass, silica, zirconium oxide, titanium oxide, agarose, polymethacrylate, polyacrylate, polyacrylamide, polyvinyl alcohol, polystyrene or derivatives thereof.

* * * * *